(12) United States Patent
Reedy et al.

(10) Patent No.: US 6,331,632 B1
(45) Date of Patent: Dec. 18, 2001

(54) CYANINE DYE PHOSPHORAMIDITES

(75) Inventors: M. Parameswara Reedy; Firdous Farooqui, both of Brea; Maged A. Michael, Placentia, all of CA (US)

(73) Assignee: Beckman Coulter, Inc., Fullerton, CA (US)

( * ) Notice: Subject to any disclaimer, the term of this patent is extended or adjusted under 35 U.S.C. 154(b) by 0 days.

(21) Appl. No.: 09/710,575

(22) Filed: Nov. 9, 2000

(51) Int. Cl.[7] ............... C07D 277/60; C07D 417/00; C07D 513/04; C07D 513/14; C07D 513/22

(52) U.S. Cl. ............... 548/148; 548/148; 548/156; 548/465; 548/469; 544/212; 544/83; 544/113; 430/541; 435/6

(58) Field of Search ................ 548/148, 156, 548/465, 469; 544/212, 83, 113; 430/541; 435/6

(56) References Cited

U.S. PATENT DOCUMENTS

| 4,981,977 | 1/1991 | Southwick et al. | 548/455 |
| 5,556,959 | 9/1996 | Brush et al. | 536/25.32 |
| 5,569,587 | 10/1996 | Waggoner | 435/6 |
| 5,571,388 | 11/1996 | Patonay et al. | 204/461 |
| 5,627,027 | 5/1997 | Waggoner | 435/6 |
| 5,808,044 | 9/1998 | Brush et al. | 536/25.32 |
| 6,048,982 * | 4/2000 | Waggoner | 548/148 |

FOREIGN PATENT DOCUMENTS

| 0 670 374 B1 | 5/1988 | (EP) . |
| 0 753 584 A1 | 1/1997 | (EP) . |

OTHER PUBLICATIONS

G. A. Reynolds, et al., "Stable Heptamethine Pyrylium Dyes that Absorb in the Infrared," J. Org. Chem., vol. 42, No. 5, pp. 885–888, 1977.

(List continued on next page.)

*Primary Examiner*—Jezia Riley
(74) *Attorney, Agent, or Firm*—William H. May; Arnold Grant; Hogan & Hartson, LLP

(57) ABSTRACT

This invention provides dye phosphoramidites, particularly phosphoramidites of cyanine and related dyes, of the general formula:

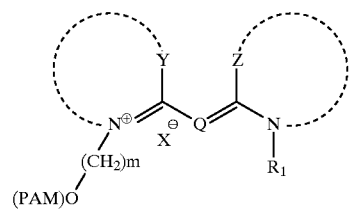

In this formula, each dotted line represents carbon atoms necessary to form a fused substituted or unsubstituted aromatic ring; m is an integer from 1 to 18; Y and Z are independently selected from the group consisting of S, O, N, $CH_2$ and $C(CH_3)_2$; $R_1$ is an alkyl; (PAM) is a phosphoramidite group; $X^\ominus$ is a negative ion; and Q is

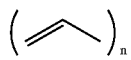

or

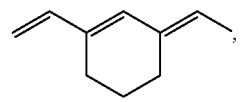

wherein n is 1, 2 or 3. Methods of making and using the dye phosphoramidites are also provided.

43 Claims, 13 Drawing Sheets

OTHER PUBLICATIONS

Lucjan Strekowski, et al., "Substitution Reactions of Nucleofugal Group in Heptamethine Cyanine Dyes. Synthesis of an Isothiocyanato Derivative for Labeling of Proteins with a Near–Infrared Chromophore," J. Org. Chem. vol. 67, No. 17, pp. 4578–4580, 1992.

Narasimhachir Narayana, et al.,"A New Method for the Synthesis of Heptamethine Cyanine Dyes: Synthesis of New Near–Infrared Fluorescent Labels," J. Org. Chem., vol. 60, No. 8, pp. 2391–2395 (w/additions and corrections page), 1995.

Lucjan Strekowski, et al., "Functionalization of Near–Infrared Cyanine Dyes," J. Heterocyclic Chem., vol. 33, pp. 1685–1688, Nov.—Dec. 1996.

Lucjan Strekowski, et al., "Facile Derivatizations of Heptamethine Cyanine Dyes," Synthetic Communications, 22(17), pp. 2593–2598, 1992.

Yu. L. Slominskii, et al., "Polymethine Dyes with Hydrocarbon Bridges. Enamino Ketones in the Chemistry of Cyanine Dyes," pp. 1854–1860. Institute of Organic Chemistry, Academy of Sciences of the Ukrainian SSR, Kiev. Translated from Zhurnal Organicheskoi Khimii, vol. 19, No. 10, pp. 2134–2142. Oct. 1983. Original article submitted Nov. 22, 1982.

Yu. L. Slominskii, et al., "Tricarbocyanines with Hydrocarbon Rings in the Chromophore," Journal of Organic Chemistry of the USSR, vol. 19, No. 10, Part 2, pp. 61–64, Oct. 1983.

Narasimhachari Narayanan, et al., "New Year Infrared Dyes for Applications in Bioanalytical Methods," SPIE,vol. 2388, pp. 6–15, Feb. 6–8, 1995.

* cited by examiner

CYANINE DYE PHOSPHORAMIDITES

BACKGROUND OF THE INVENTION

1. Area of the Art

The invention relates generally to cyanine dyes and specifically to cyanine dye phosphoramidites, their synthesis and methods of use in labeling of oligonucleotides.

2. Description of the Prior Art

Many procedures employed in biomedical research and recombinant DNA technology rely heavily on the use of oligonucleotides as probes, primers, linkers, adapters, and gene fragments. Several of these uses are described in common laboratory manuals, such as Molecular Cloning, A Laboratory Manual, Second Ed., J. Sambrook, et al., Eds., Cold Spring Harbor Laboratory Press, 1989; and Current Protocols In Molecular Biology, F. M. Ausubel, et al., Eds., Current Publications, 1993.

Oligonucleotides of a desirable sequence are synthesized by coupling nucleosides through phosphorous-containing covalent linkages. The most commonly used oligonucleotide synthesis method involves reacting a nucleoside with a protected cyanoethyl phosphoramidite monomer in the presence of a weak acid; oxidation of the formed phosphite linkage; and hydrolysis of the cyanoethyl group (Advances in the Synthesis of Oligonucleotides by the Phosphoramidite Approach, Beaucage, S. L.; Iyer, R. P., Tetrahedron, 1992, 48, 2223–2311).

Many applications, such as automated DNA sequencing and mapping, in situ detection of hybridization, detection of PCR products, and structural studies, require labeled oligonucleotides. While radioactive labels were traditionally used in these applications, recently certain cyanine dyes have proved to be extremely fluorescent and quite useful in the labeling of biomolecules.

Cyanine dyes offer many desirable properties, including safe handling, absorbency at longer wavelengths, high extinction coefficient, relatively high quantum efficiency, small molecular size, ease of chemical manipulation, and reasonable stability to reagents, pH and temperature. Because of a low background fluorescence of biological materials and a high absorbency of cyanine dyes in the longer wavelength portion of the spectrum, cyanine dyes provide excellent signal-to-noise ratios. By synthesizing structural modifications of the chromophore portion of cyanine dyes, different fluorescent labeling reagents absorbing and emitting in a broad spectrum range from 400 to nearly 1100 nm can be obtained. The versatility of functional groups that can be incorporated into cyanine dyes permits control over the solubility of the dye and labeled product, and helps reduce non-specific binding of the labeled materials to irrelevant components in an assay mixture (Waggoner, U.S. Pat. No. 5,569,587 and U.S. Pat. No. 5,627,027).

At present, labeling of oligonucleotides with cyanine dyes is performed by a manual, two-step procedure. First, an oligonucleotide is synthesized and, then, an activated cyanine dye is linked to the 5' end of the synthesized oligonucleotide. Usually, cyanine dyes are activated by an introduction of reactive groups that assist in covalent attachment of cyanine dyes to oligonucleotides (see, for example, U.S. Pat. Nos. 5,569,587 and 5,627,027). This two-step method is slow (4–5 days), tedious, expensive, and often produces undesirable organic by-products.

In an alternative, more convenient, one-step approach, a fluorescent dye is converted into a phosphoramidite and is used in direct labeling of an oligonucleotide during its synthesis. However, currently available phosphoramidites of cyanine dyes are substantially more expensive and less stable than their standard, unmodified counterparts.

U.S. Pat. No. 5,556,959 ('959) discloses the use of carbocyanine phosphoramidites to label synthetic oligonucleotides. The cyanine phosphoramidites of the '959 patent, however, contain protecting groups, such as trityl; 4-O-monomethoxytrityl; 4,4'-O-dimethoxytrityl or acyl. Protecting groups are usually associated with instability during storage and handling, thus making these phosphoramidites less valuable commercially.

SUMMARY OF THE INVENTION

In view of deficiencies of the related art, it is an object of the present invention to provide stable cyanine dye phosphoramidites for direct labeling of oligonucleotides during their automated synthesis on DNA synthesizers. It is also an object of the present invention to provide convenient methods for synthesizing phosphoramidites that do not require steps of introduction and removal of protecting groups. It is a further object of the present invention to provide a method for labeling an oligonucleotide directly during its synthesis.

These and other objects are achieved in dyes of the present invention having a following general formula:

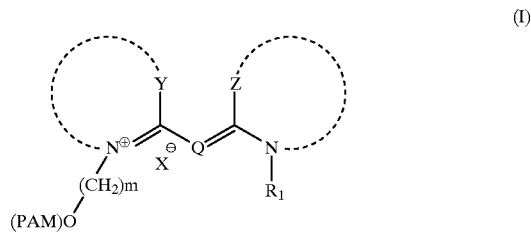

(I)

wherein each dotted line represents carbon atoms necessary to form a fused substituted or unsubstituted aromatic ring; m is an integer from 1 to 18; Y and Z are independently selected from the group consisting of S, O, N, $CH_2$ and $C(CH_3)_2$; $R_1$ is an alkyl; (PAM) is a phosphoramidite group; $X^{\ominus}$ is a negative ion; and Q is

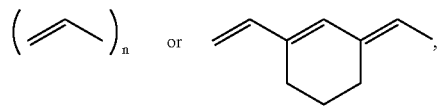

wherein n is 1, 2, or 3.

According to one embodiment of the present invention, the dye is a cyanine dye selected from the group consisting of Cy5, benz Cy5, dibenz Cy5, Cy7, benz Cy7, dibenz Cy7, cyclic Cy7, cyclic benz Cy7, and cyclic dibenz Cy7. The phosphoramidite group may be a N,N-diisopropyl-O-β-cyanoethyl phosphoramidite group.

Another aspect of the present invention provides a method of synthesizing a dye phosphoramidite. The method includes the steps of:

(a) forming a hydroxy derivative of the dye having a formula:

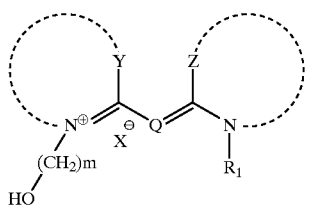
(II)

wherein each dotted line represents carbon atoms necessary to form a fused substituted or unsubstituted aromatic ring; m is an integer from 1 to 18; Y and Z are independently selected from the group consisting of S, O, N, $CH_2$ and $C(CH_3)_2$; $R_1$ is an alkyl; $X^\ominus$ is a negative ion; and Q is

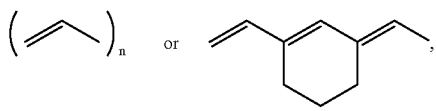

wherein n is 1, 2 or 3; and (b) replacing hydrogen of the OH group with a phosphoramidite group.

According to embodiments of the present invention, the dye can be a cyanine dye, and particularly Cy5, benz Cy5, dibenz Cy5, Cy7, benz Cy7, dibenz Cy7, cyclic Cy7, cyclic benz Cy7, or cyclic dibenz Cy7. The phosphoramidite group may be a N,N-diisopropyl-O-β-cyanoethyl phosphoramidite group.

In one embodiment of the present invention, the step of forming a hydroxy derivative of the dye (II) comprises reacting compounds (XI), (XII) and (XIII) under conditions that allow formation of the hydroxy derivative of the cyanine dye.

Compound (XI) may be any compound having a general formula:

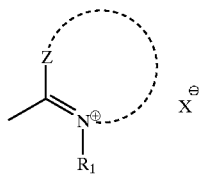

Compound (XII) may be any compound having a general formula: Ph—$R_3$—Ph, wherein Ph is phenyl and $R_3$ is:

N=CH—$CH_2$—CH=N,

or

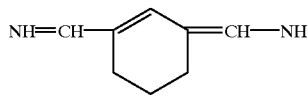

Compound (XIII) may be any compound having a general formula:

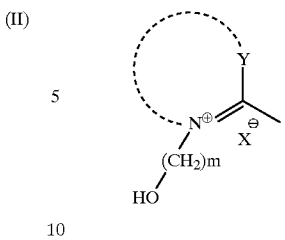

wherein each dotted line represents carbon atoms necessary to form a fused substituted or unsubstituted aromatic ring; m is an integer from 1 to 18; Y and Z are independently selected from the group consisting of S, O, N, $CH_2$ and $C(CH_3)_2$; $R_1$ is an alkyl; and $X^\ominus$ is a negative ion.

Alternatively, the step of forming a hydroxy derivative of the dye may comprise:

(a1) forming an acetoxy derivative of the dye having a formula:

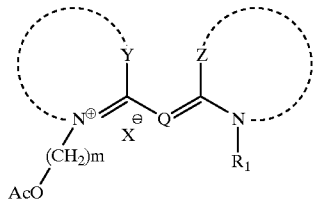
(XX)

wherein each dotted line represents carbon atoms necessary to form a fused substituted or unsubstituted aromatic ring; m is an integer from 1 to 18; Y and Z are independently selected from the group consisting of S, O, N, $CH_2$ and $C(CH_3)_2$; $R_1$ is an alkyl; $X^\ominus$ is a negative ion; and Q is

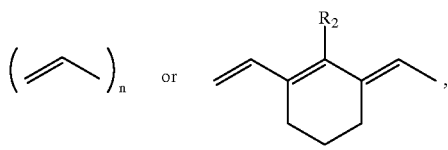

wherein n is 1 or 2 and $R_2$ is a halogen or hydrogen; and (a2) converting AcO group of the dye into the OH group.

A further aspect of the present invention provides a method wherein luminescent dye phosphoramidites are used to label oligonucleotides directly.

The present invention provides both economic and technical advantages over the use of other dyes in the labeling of biopolymers, especially oligonucleotides. As explained in detail below, dye phosphoramidites of this invention can be used directly on any DNA synthesizer, for example, oligo 1000M (Beckman Coulter, Calif.), to automatically add the dye to the oligonucleotide during its synthesis. By using dye phosphoramidites with no protecting groups, the total time for the preparation of a labeled oligonucleotide is greatly reduced, since the step of removing a protecting group is eliminated. By incorporating a cyclic moiety into the chain of conjugated double bonds of Cy7 and DBCy7 phosphoramidites, their partial conversion into Cy5-like species is effectively prevented and stable dyes are formed. In addition to cost and time saving provided by utilizing dye phosphoramidites of this invention for labeling of oligonucleotides, higher over-all yield of labeled product is also achieved as compared to the conventional two-step method.

The invention is defined in its fullest scope in the appended claims and is described below in its preferred embodiments.

DESCRIPTION OF THE FIGURES

The above-mentioned and other features of the present invention and the manner of obtaining them will become more apparent, and will be best understood, by reference to the following description, taken in conjunction with the accompanying drawings, in which.

DETAILED DESCRIPTION OF THE INVENTION

Figure 1A:
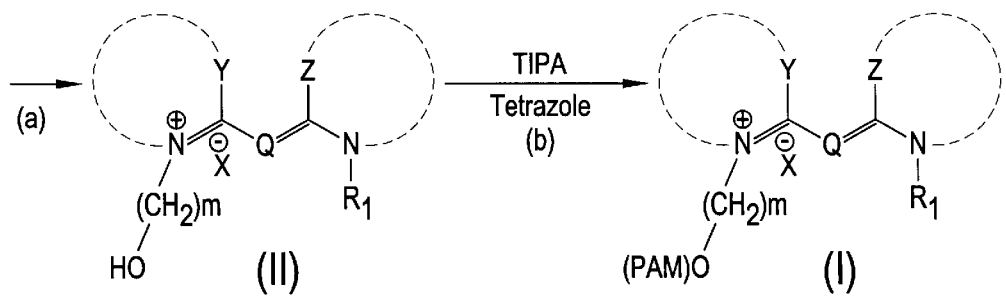
FIGS. 1A, 1B, and 1C schematically illustrate methods of synthesis of dye phosphoramidites of the present invention.

In order to facilitate a direct introduction of dye labels into oligonucleotides during their synthesis, the present invention provides a dye phosphoramidite, having a formula:

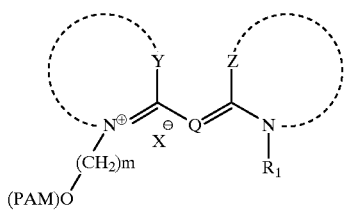

(I)

In this formula, each dotted line represents carbon atoms necessary to form a fused substituted or unsubstituted aromatic ring; m is an integer from 1 to 18; Y and Z are independently selected from the group consisting of S, O, N, $CH_2$ and $C(CH_3)_2$; $R_1$ is an alkyl; (PAM) is a phosphoramidite group; $X^\ominus$ is a negative ion; and Q is

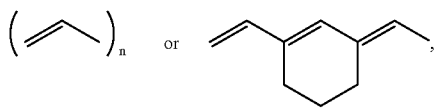

or wherein n is 1, 2 or 3.

The activated dyes can contain a heterocyclic ring, a single ring aromatic structure, such as a phenyl ring, or a fused ring structure, such as a naphthyl ring. The alkyl group generally possesses one to eighteen carbon atoms, preferably two carbon atoms. The phosphoramidite group is usually attached to the dye with an alkyl chain. The length of the alkyl chain is preferably about 1 to 12 carbon atoms long. The most practical alkyl chain length is about 6 carbon atoms long. The Compound (I) of the present invention includes a negative ion $X^\ominus$ Preferably, this ion is a halide, although other negative ions may be used. For example, the negative ion may be $I^\ominus$ or $Br^\ominus$, depending on the synthesis strategy. The phosphoramidite group may be a N,N-diisopropyl-O-β-cyanoethyl phosphoramidite group, although other phosphoramidite known to one skilled in the art may also be used.

Generally speaking, the dyes of the present invention can be any of the fluorescent dyes commonly used for labeling purposes, as long as they incorporate a phosphoramidite group and an alkyl group. It is also required that the phosphoramidite group and the alkyl group are attached to nitrogens in the indole or benzoindole portion of the dye. The absorption and emission wavelengths of the dye are not restricted to a particular region of the spectrum but may be anywhere from the near UV through the near IR region or beyond these extremes. According to embodiments of the present invention, the dyes may be cyanine and related dyes.

Cyanine dyes have several desirable properties to serve as sensitive detection labels, including absorption at longer wavelengths (which translates into the use of inexpensive detection systems and low background from biological samples at these wavelengths), high extinction coefficient, relatively high quantum efficiency, small molecular size, ease of chemical manipulation without compromising the fluorescence characteristics, and reasonable stability to reagents, pH and temperature.

The cyanine dyes have a general structure where the chromophore of the cyanine dyes is composed of a series of conjugated double bonds, having two quaternary nitrogen atoms at the terminal ends which share one positive charge. According to the number of central double bonds, the cyanine dyes can be classified as monocarbocyanine (n=1, also known as trimethinecarbocyanine), dicarbocyanine (n=2, also known as pentamethinecarbocyanine), and tricarbocyanine (n=3, also known as heptamethinecarbocyanine). The number of central double bonds determines, in part, the excitation wavelength. Often, higher values of n contribute to increased luminescence and absorbency. At values of n above 4, the compound becomes unstable. Thereupon, further luminescence can be imparted by modifications at the ring structures. When n=2, the excitation wavelength is about 650 nm and the compound is very fluorescent.

In one embodiment of this invention, phosphoramidites of dicarbocyanine dyes (Cy5, benz Cy5 (BCy5) and dibenz Cy5 (DBCy5)) and tricarbocyanine dyes (Cy7, benz Cy7 (BCy7) and dibenz Cy7 (DBCy7)) are used for direct labeling. The difference between these two groups of dyes is the presence of an additional double bond in Cy7, BCy7, and DBCy7 relative to Cy5, BCy5, and DBCy5, respectively. Consequently, the dicarbocyanine dyes have absorption and emission maxima about 100 nm shorter than their tricarbocyanine counterparts. The benzoindole cyanines, BCy5 and BCy7, have one benzene group substitution and DBCy5 and DBCy7 have two extra benzene group substitutions relative to the corresponding indole cyanines, Cy5 and Cy7. As such, benzoindole cyanines have absorption and emission maxima longer than their indole counterparts.

In another embodiment of this invention, phosphoramidites of cyclic Cy7 and DBCy7 dyes are utilized. It is a discovery of the present invention that the introduction of a cyclic moiety into the chain of conjugated double bonds of cyanine dye molecules provides an extra stability to Cy7 species. In one embodiment, cyclic moiety having the following structure may be used:

The dye phosphoramidites of the present invention can be used directly on any DNA synthesizer to automatically add the dye to the oligonucleotide. The dye phosphoramidites of this invention do not contain any protecting groups, which makes them more stable. By the use of dye phosphoramidites with no protecting groups, the total time for the preparation of a labeled oligonucleotide is greatly reduced, since the step of removing a protecting group is eliminated. In addition to cost and time saving provided by utilizing dye phosphoramidites of this invention for labeling of oligonucleotides, higher over-all yield of labeled product is also achieved as compared to the conventional two-step method.

Figure 1B:
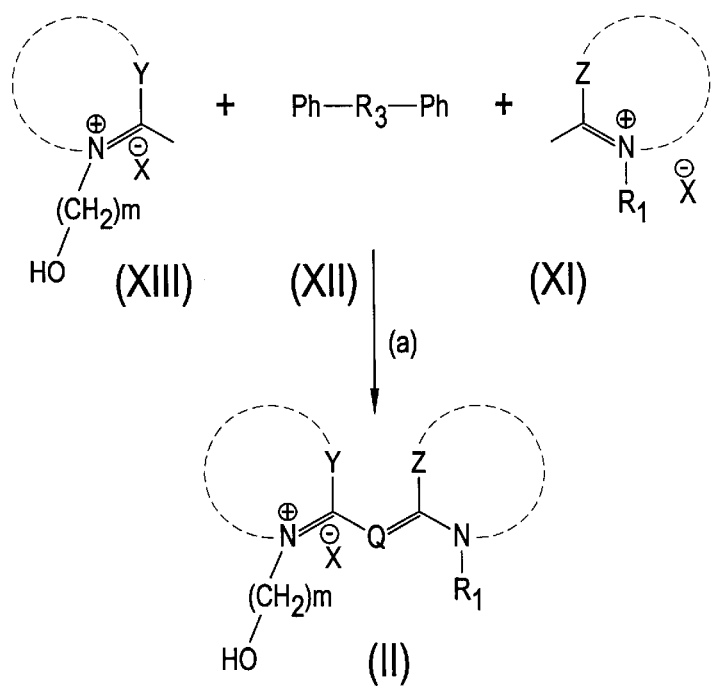
Figure 1C:
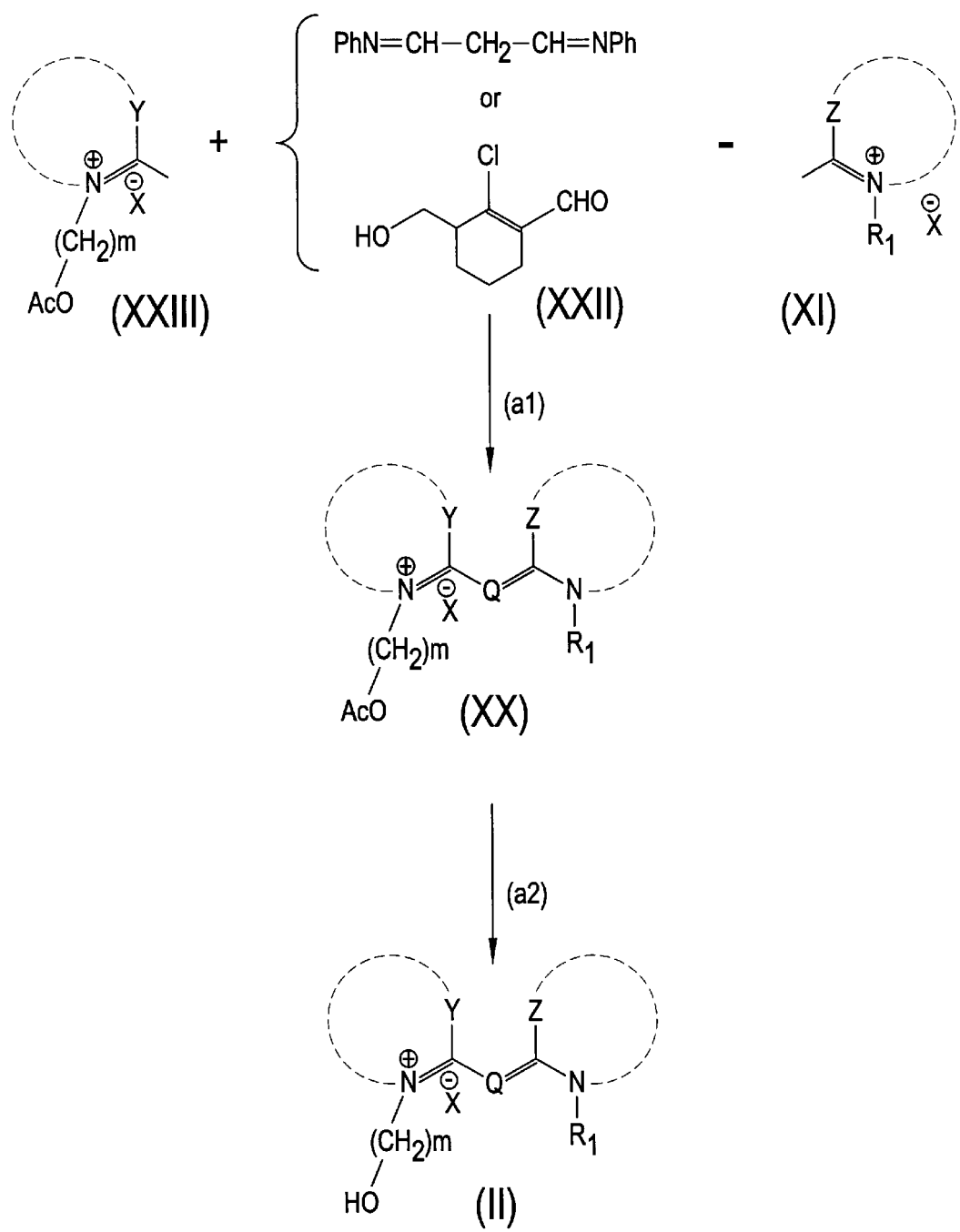

Another aspect of the present invention provides a method of synthesizing a dye phosphoramidite. The general synthetic scheme for the preparation of a dye phosphoramidite of the present invention is shown in FIGS. 1A–1C. The method includes the steps of:

(a) forming a hydroxy derivative of the dye (II), having a formula:

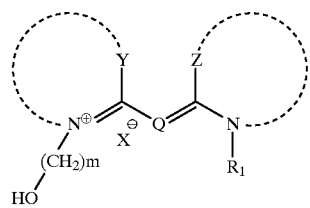

wherein each dotted line represents carbon atoms necessary to form a fused substituted or unsubstituted aromatic ring; m is an integer from 1 to 18; Y and Z are independently selected from the group consisting of S, O, N, $CH_2$ and $C(CH_3)_2$; $R_1$ is an alkyl; $X^{\ominus}$ is a negative ion; and Q is

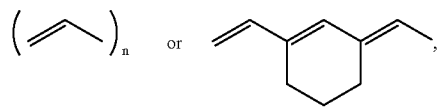

wherein n is 1, 2 or 3; and (b) replacing hydrogen of the OH group with a phosphoramidite group.

The dyes can contain a heterocyclic ring, a single ring aromatic structure, such as a phenyl ring, or a fused ring structure, such as a naphthyl ring. Of particular interest are the cyanines discussed above, including Cy5, BCy5, DBCy5, Cy7, BCy7, DBCy7, cyclic Cy7, cyclic BCy7, and cyclic DBCy7.

For the purpose of this invention, the hydroxy derivative of the dye (II) is reacted with a suitable reagent under conditions that are sufficient to form a dye phosphoramidite (I). In accordance with the present invention and as shown in FIG. 1A, suitable reagents for replacing hydrogen with a phosphoramidite group include, but are not limited to, a mixture of tetrazole with $(iPr_2N)_2PO$—$CH_2$—$CH_2$—CN. Other reagents, such as $iPr_2N$—$P(Cl)OCH_2CH_2CN$ may also be used. In accordance with one embodiment, this reaction may preferably be carried out at −20° C. and under inert atmosphere.

In accordance with embodiments of the present invention, the step (a) of forming a hydroxy derivative of a cyanine dye may be carried out in two alternative ways, as shown in FIGS. 1B and 1C.

In the first method shown in FIG. 1B, the step of forming a hydroxy derivative of the cyanine dye involves reacting compounds (XI), (XII) and (XIII) under conditions that allow the formation of the hydroxy derivative of the cyanine dye.

Compound (XI) may be any compound having a general formula:

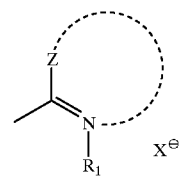

Compound (XII) may be any compound with a general formula: Ph—$R_3$—Ph, wherein Ph is phenyl and $R_3$ is:

 (XIIa)

 (XIIb)

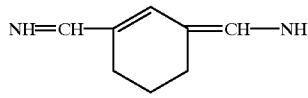 (XIIc)

Compound (XIII) may be any compound with a general formula:

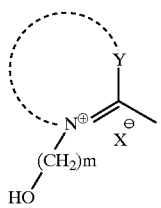

Each dotted line in the above formulas represents carbon atoms necessary to form a fused substituted or unsubstituted aromatic ring. In the above formulas, m is an integer from 1 to 18; Y and Z are independently selected from the group consisting of S, O, N, $CH_2$ and $C(CH_3)_2$; $R_1$ is an alkyl; and $X^\ominus$ is a negative ion. In one embodiment, the negative ion is a bromide.

Figure 2:
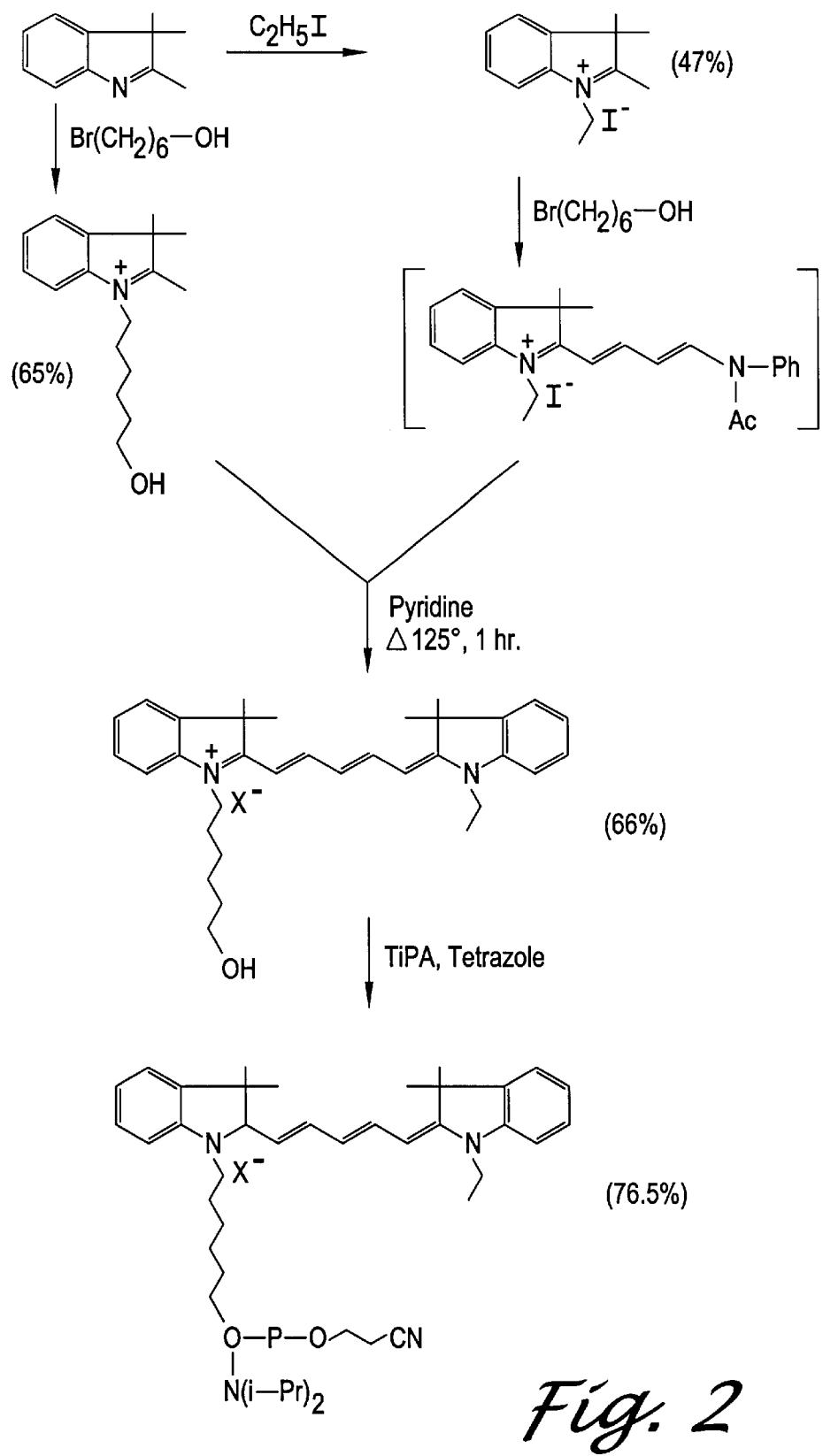
FIG. 2 shows a reaction scheme, illustrating synthesis of Cy5 phosphoramidites of the present invention.
Figure 3:
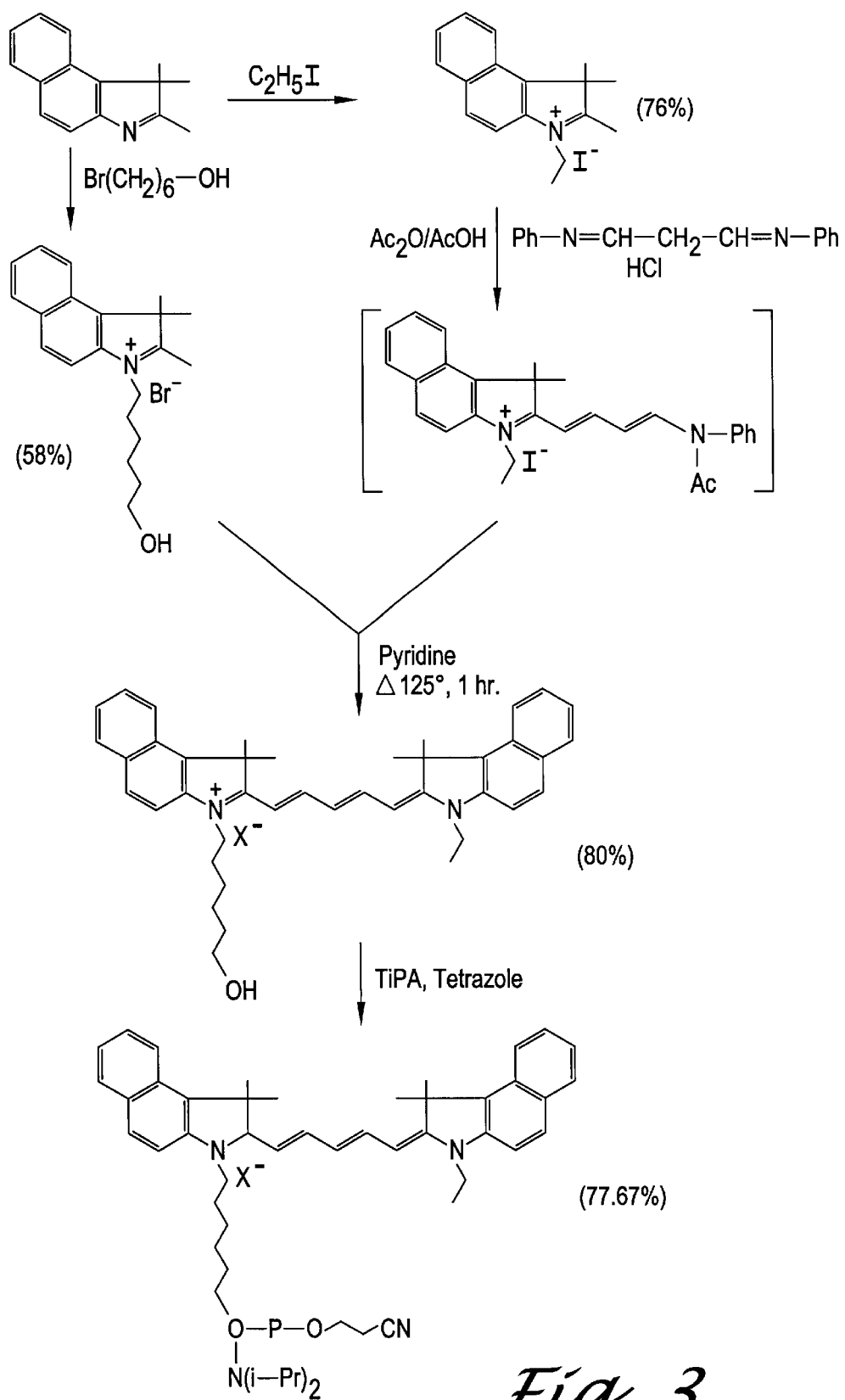
FIG. 3 shows a reaction scheme, illustrating synthesis of DBCy5 phosphoramidite of the present invention.
Figure 7:
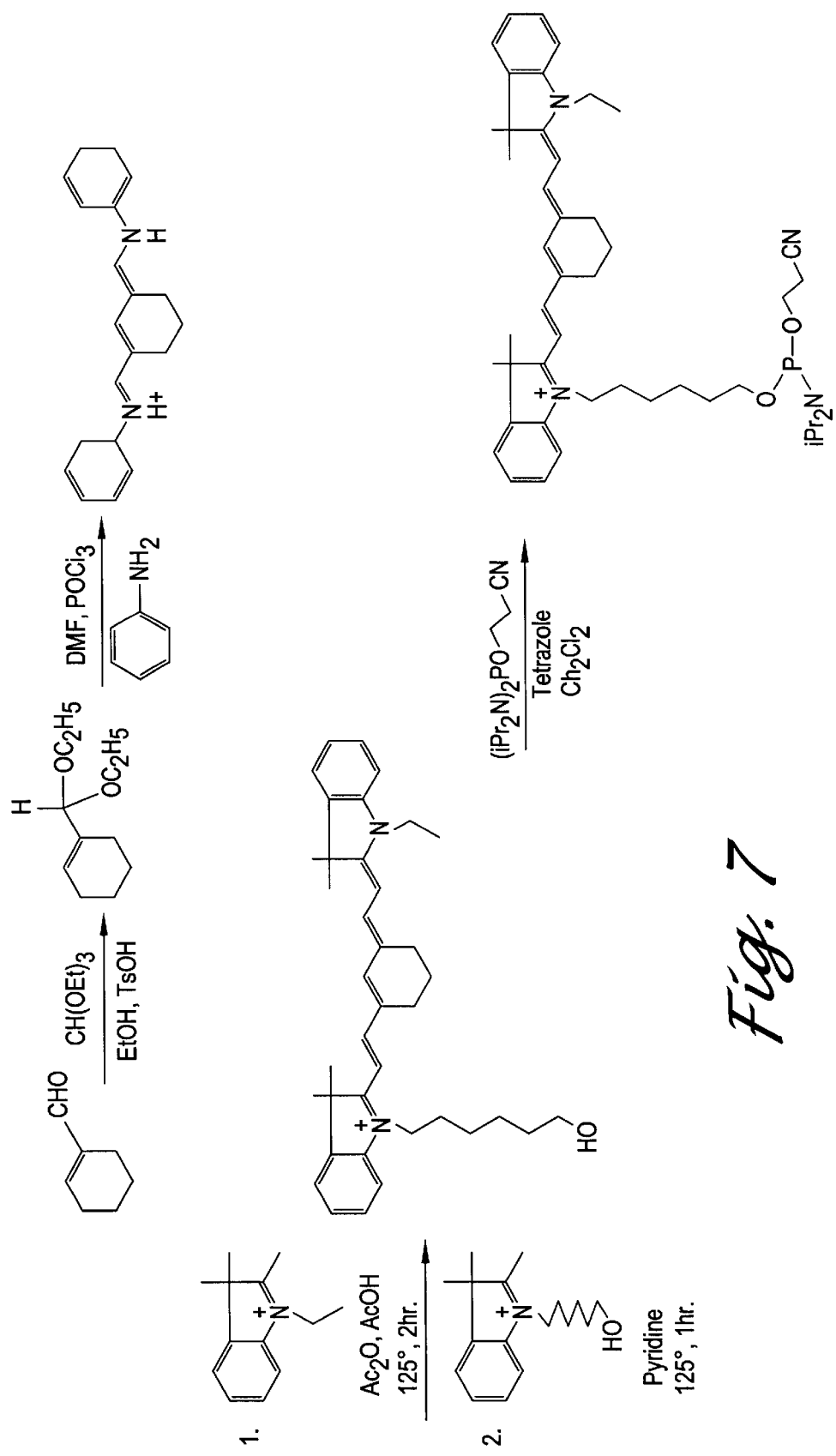
FIG. 7 shows a reaction scheme, illustrating synthesis of cyclic Cy7 phosphoramidite of the present invention.
Figure 8:
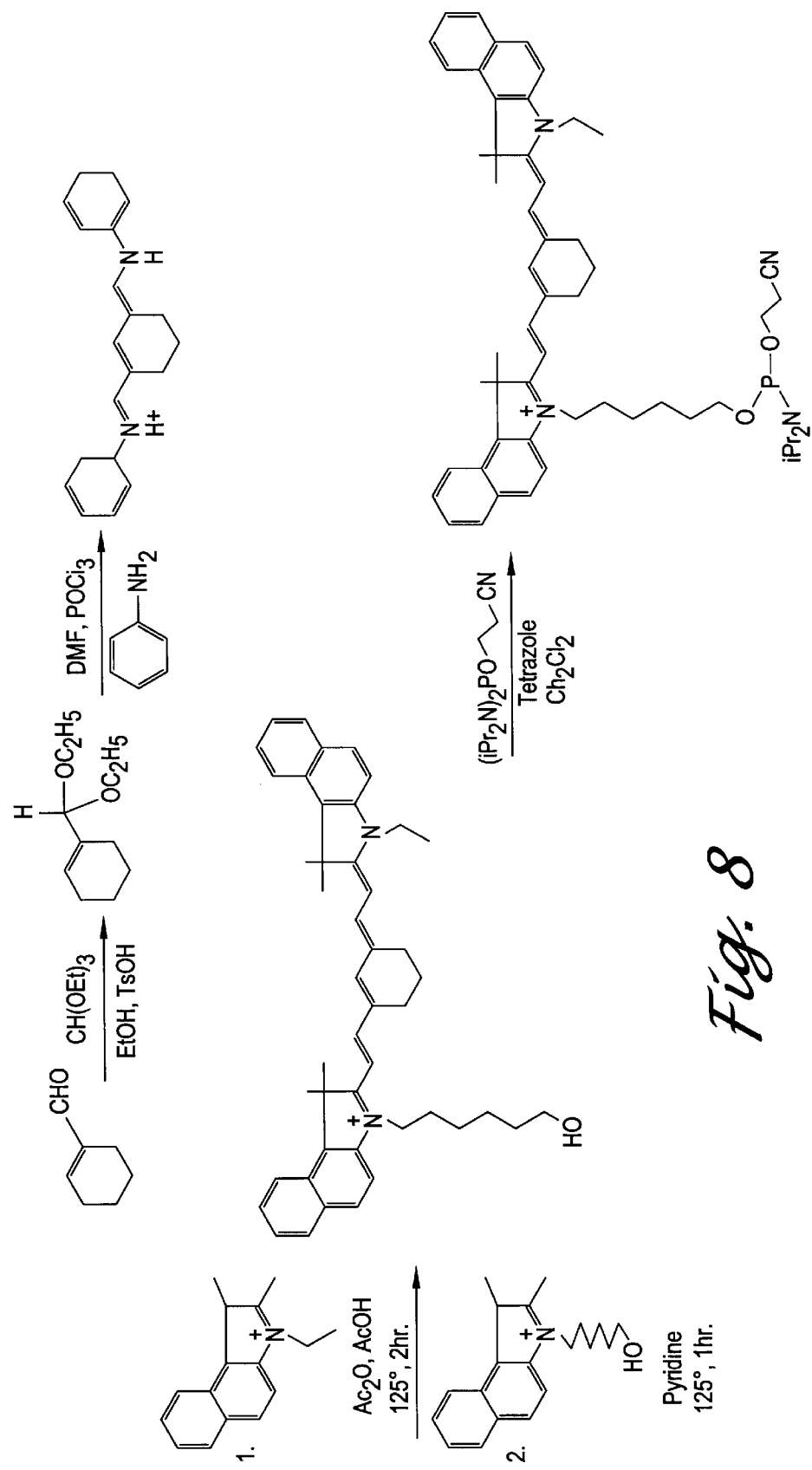
FIG. 8 shows a reaction scheme, illustrating synthesis of cyclic DBCy7 phosphoramidite of the present invention.

The choice of particular Compounds (XI), (XII), and (XIII) depends on the type of the dye phosphoramidite to be synthesized. For example, in order to synthesize a Cy5 phosphoramidite, one may use Compound (XIIa) and unsubstituted Compounds (XI) and (XIII) (FIG. 2). For synthesis of cyclic Cy7 phosphoramidite, one may use Compound (XIIc) and unsubstituted Compounds (XI) and (XIII) (FIG. 7). In order to synthesize DBCy5 phosphoramidite, Compound (XIIa) and benz-substituted Compounds (XI) and (XIII) may be employed (FIG. 3). Finally, cyclic DBCy7 phosphoramidite may be synthesized by utilizing benz-substituted Compounds (XI) and (XIII) and Compound (XIIc) (FIG. 8). Those skilled in the art will appreciate that other phosphoramidites may be synthesized by choosing the appropriate compounds (XI), (XII), and (XIII).

While any compounds with general formulas (XI) and (XIII) may be used according to the method shown in FIG. 1B, in one embodiment Compound (XI) is 1-ethyl 2,3,3-trimethyl-(3H)-indolinium iodide and Compound (XIII) is 1-(6-hydroxyhexyl)-1,1,2-trimethyl-(3H)-indolinium bromide. In this embodiment, depending on the type of Compound (XII) used, phosphoramidites of unsubstituted cyanine dyes, such as Cy5 (FIG. 2), Cy7 or cyclic Cy7 (FIG. 7), are obtained. When Compound (XIIa) is used, a phosphoramidite of Cy5 is obtained. Similarly, with Compound (XIb), a phosphoramidite of Cy7 is produced and, with Compound (XIIc), a phosphoramidite of cyclic Cy7 is formed.

In another embodiment, Compound (XI) is 1-ethyl 1,1,2-trimethyl-H-Benz(e)indolinium iodide and Compound (XIII) is 1-(6-hydroxyhexyl)-1,1,2-trimethyl-H-Benz(e)indolinium bromide. In this embodiment, depending on the type of Compound (XII) used, phosphoramidites of benzene-substituted cyanine dyes, such as DBCy5 (FIG. 3), DBCy7 or cyclic DBCy7 (FIG. 8), are synthesized. When Compound (XIIa) is used, a phosphoramidite of DBCy5 is obtained. Similarly, with Compound (XIIb), a phosphoramidite of DBCy7 is produced and, with Compound (XIIc), a phosphoramidite of cyclic DBCy7 is formed.

While various agents can be used for forming Compound (XIII), in one embodiment, Compound (XIII) is formed by reacting Compound (XIV) with $Br(CH_2)_m$—OH under reaction conditions that allow the formation of Compound (XIII). Compound (XIV) can be any compound having a general formula:

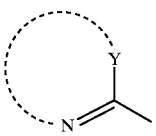

The dotted line represents carbon atoms necessary to form a fused substituted or unsubstituted aromatic ring. Y is selected from the group consisting of S, O, N, $CH_2$ and $C(CH_3)_2$; and m is an integer from 1 to 18. For example, as shown in FIGS. 2 and 3, Compound (XIV) is 1,1,2-trimethyl-(3H)-indole or 1,1,2-trimethyl-H-Benz(e)-indole, correspondingly. Different reaction conditions may be used as long as they allow the formation of the Compound (XIV). For example, the reactions shown in FIGS. 2 and 3 were carried out at 125° C.

The successful synthesis of the hydroxy derivative of a dye, in accordance with the method depicted in FIG. 1B, also depends on reaction conditions. In one embodiment, Compound XI and Compound XII are heated in acetic anhydride and acetic acid for 30 minutes at 125° C. The resulting intermediate is evaporated to dryness and washed three times with 50 ml of diethyl ether and then reacted with Compound XIII in pyridine at 125° C. for 30 minutes. Examples 1 and 2 provide further details on suitable reaction conditions. Other reaction conditions may be also used as long as they support the formation of the hydroxy derivative (II).

In an alternative method, one may synthesize hydroxy derivative of the dye (II) in accordance with the method shown in FIG. 1C. The method comprises:

(a1) forming an acetoxy derivative of the dye (XX), having a formula:

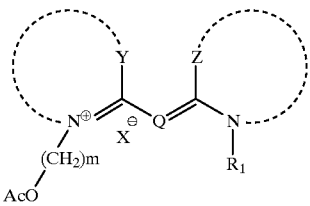

and (a2) converting AcO group of the cyanine dye into the OH group.

In formula (XX), each dotted line represents carbon atoms necessary to form a fused substituted or unsubstituted aromatic ring; m is an integer from 1 to 18; Y and Z are independently selected from the group consisting of S, O, N, $CH_2$ and $C(CH_3)_2$; $R_1$ is an alkyl; $X^\ominus$ is a negative ion; and Q is

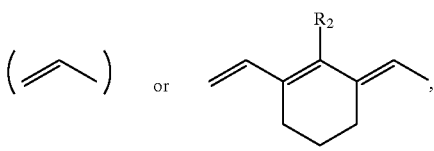

wherein n is 1 or 2 and

R$_2$ is a halogen or hydrogen. In one embodiment, the negative ion is I$^\ominus$. The dyes can contain a heterocyclic ring, a single ring aromatic structure, such as a phenyl ring, or a fused ring structure, such as a naphthyl ring. Of particular interest are the cyanines discussed above, including Cy5, BCy5, and DBCy5, cyclic Cy7, cyclic BCy7, and cyclic DBCy7.

While most of phosphoramidites may be obtained using this method, certain difficulties exist in synthesizing Cy7-type cyanine dyes using this strategy, since Cy7 dyes are not stable and often decompose into Cy5-type species during storage or manipulation. It is a discovery of the present invention, that when a stabilizing group, such as a cyclic group having structure

is introduced into the chain of conjugated double bonds of cyanine dye molecule, the Cy7 species becomes more stable and their phosphoramidites may be synthesized according to the method disclosed in FIG. 1C. Alternatively, unmodified Cy7-type phosphoramidites can be obtained, according to the method shown in FIG. 1B, as explained above.

While different strategies may be used to carry out step (a1) of forming an acetoxy derivative of the dye (XX), in one embodiment, this step includes reacting compounds (XI), (XXII) and (XXIII) under conditions that allow the formation of the acetoxy derivative of the cyanine dye. In this embodiment, Compound (XI) may be any compound having a general formula:

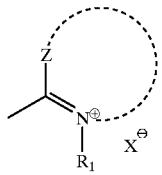

Compound (XXII) may be any compound having a general formula:

(XXIIa)

PhN=CH—CH$_2$—CH=NPh

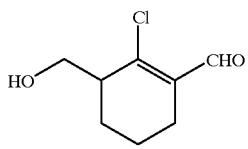

wherein Ph is phenyl.

Compound (XXIII) may be any compound with a general formula:

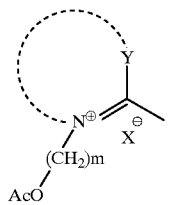

Each dotted line represents carbon atoms necessary to form a fused substituted or unsubstituted aromatic ring; m is an integer from 1 to 18; Y and Z are independently selected from the group consisting of S, O, N, CH$_2$ and C(CH$_3$)$_2$; R$_1$ is an alkyl; and X$^\ominus$ is a negative ion. In one embodiment, the negative ion is I$^\ominus$.

Figure 9:
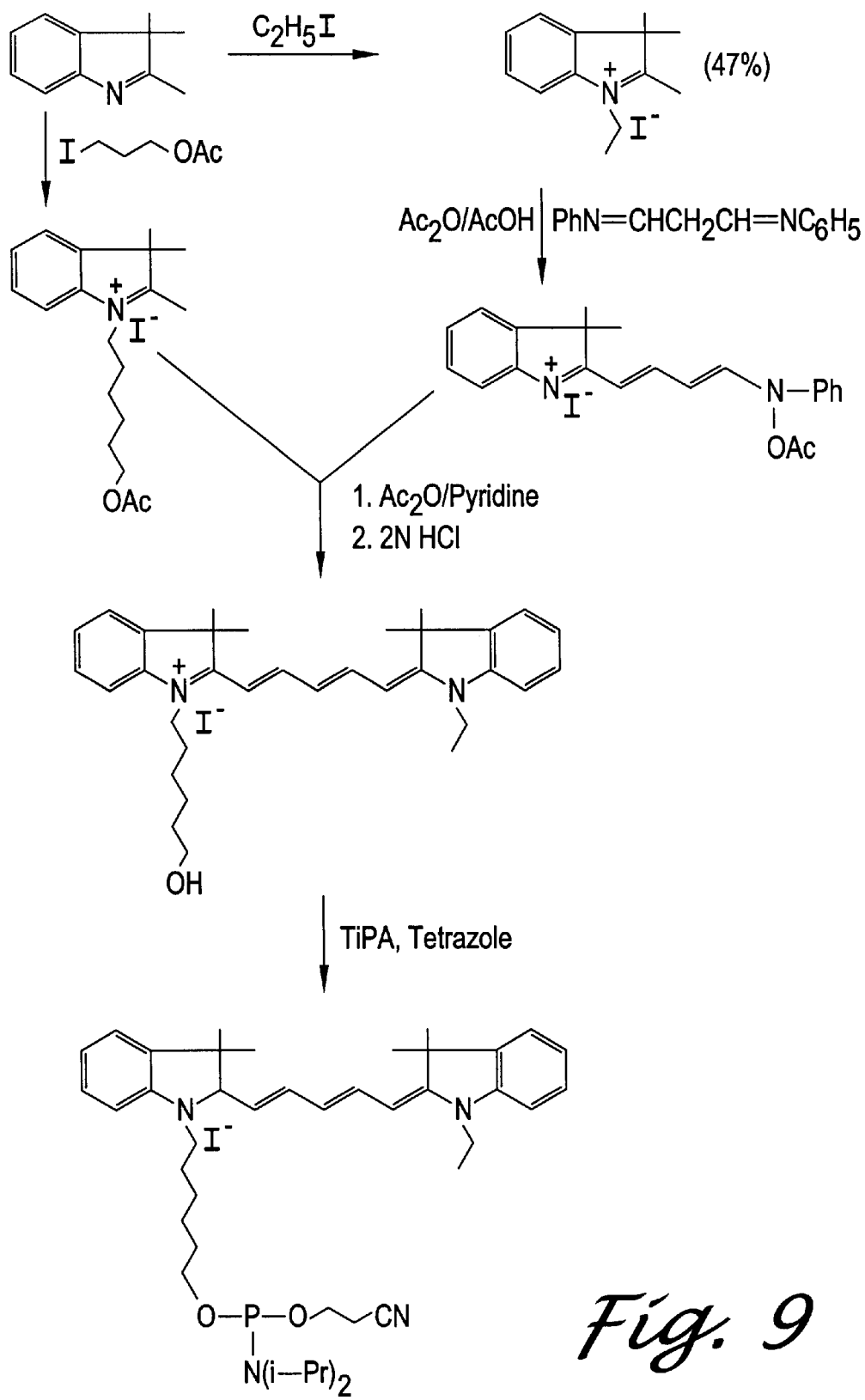
FIG. 9 shows a reaction scheme, illustrating synthesis of Cy5 phosphoramidite of the present invention.
Figure 11:
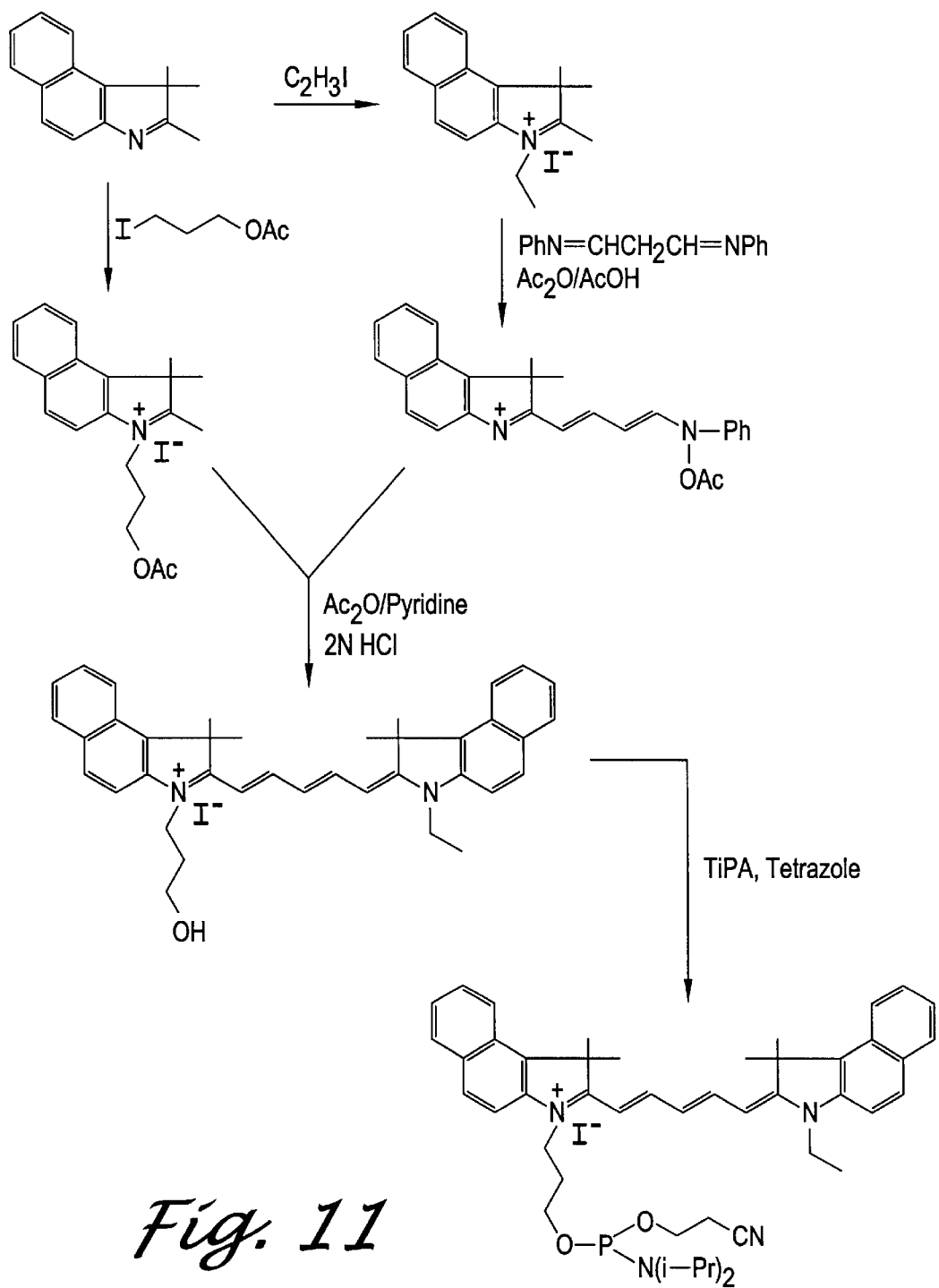
FIG. 11 shows a reaction scheme, illustrating synthesis of DBCy5 phosphoramidite of the present invention.
Figure 12:
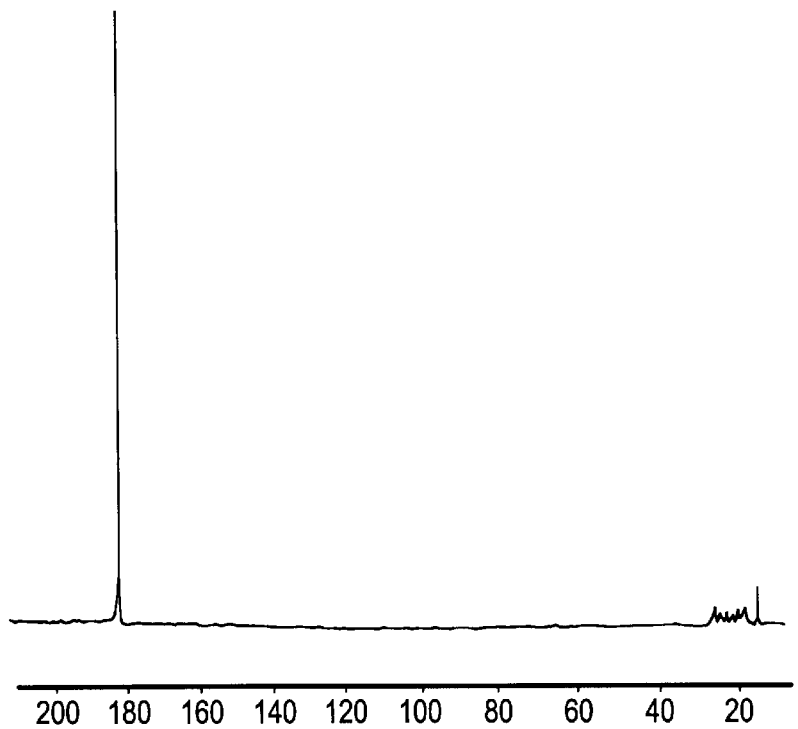
FIG. 12 depicts $^{31}$P NMR spectra of the DBCy5 phosphoramidite obtained according to the reaction scheme of FIG. 11.
Figure 13:
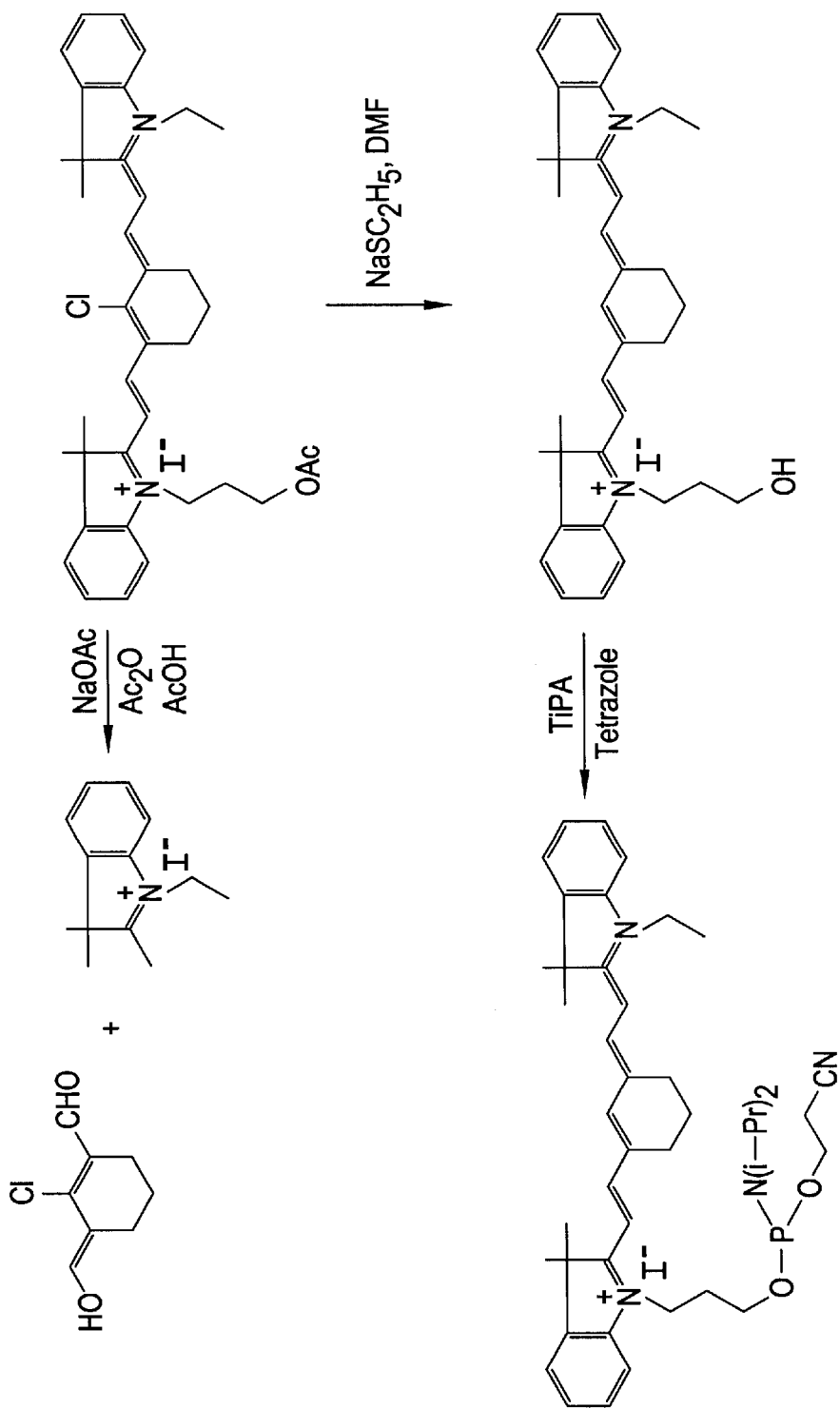
FIG. 13 shows a reaction scheme, illustrating synthesis of cyclic Cy7 phosphoramidite of the present invention.

Similarly to the method shown in FIG. 1B, the choice of particular Compounds (XI), (XXII), and (XXIII) depends on the type of the dye phosphoramidite to be synthesized. For example, in order to synthesize a Cy5 phosphoramidite, one may use Compound (XXIIa) and unsubstituted Compounds (XI) and (XXIII) (FIG. 9). For synthesis of cyclic Cy7 phosphoramidite, one may use Compound (XXIIb) and unsubstituted Compounds (XI) and (XXIII) (FIG. 13). In order to synthesize DBCy5 phosphoramidite, Compound (XXIIa) and benz-substituted Compounds (XI) and (XXIII) may be employed (FIG. 11). Those skilled in the art will appreciate that, other phosphoramidites may be synthesized by choosing the appropriate Compounds (XI), (XXII), and (XXIII).

While any compounds with general formulas (XI) and (XXIII) may be used according to the method shown in FIG. 1C, in one embodiment Compound (XI) is 1-ethyl 2,3,3-trimethyl-(3H)-indolinium iodide and Compound (XXIII) is 1-(1'-acetoxypropyl)-2,3,3'-trimethyl-(3H)-indolinium iodide. In this embodiment, depending on the type of Compound (XXII) used, phosphoramidites of unsubstituted cyanine dyes, such as Cy5 (FIG. 9) or cyclic Cy7 (FIG. 13), are obtained. When Compound (XXIIa) is used, a phosphoramidite of Cy5 is obtained. Similarly, with Compound (XXIIb), a phosphoramidite of cyclic Cy7 is produced.

In another embodiment, Compound (XI) is 1-ethyl 1,1,2-trimethyl-H-Benz(e)indolinium iodide and Compound (XXIII) is 1-(1'-acetoxypropyl)-2,3,3'-trimethyl-H-Benz(e) indolinium iodide. In this embodiment, depending on the type of Compound (XXII) used, phosphoramidites of benzene-substituted cyanine dyes, such as DBCy5 (FIG. 11) or cyclic DBCy7 (not shown), are synthesized. When Compound (XXIIa) is used, a phosphoramidite of DBCy5 is obtained. Similarly, with Compound (XXIIb), a phosphoramidite of cyclic DBCy7 is formed.

The successful synthesis of the acetoxy derivative of the dye, in accordance with the method depicted in FIG. 1C, also depends on reaction conditions. In one embodiment, Compounds XI and XXII are incubated in a mixture of acetic acid (20 ml) and acetic anhydride (20 ml) in an oil bath at 120° C. for 2 hr. The solvents are removed with a rotary evaporator and the product is washed twice with 30 ml of diethyl ether (total 60 ml of diethyl ether). The obtained product is dissolved in an acetic anhydride and pyridine mixture (20 ml/20 ml), then Compound XXIII is added to the reaction mixture and the mixture is incubated at 110° C. for 30 min. The mixture is cooled and rotary evaporated to remove solvents. Examples 3 and 4 provide further details on suitable reaction conditions. Other reaction conditions may also be used as long as they support formation of the hydroxy derivative (XX).

Another aspect of this invention provides a method of labeling oligonucleotides. The method comprises the step of reacting the dye phosphoramidite of the invention described above with the oligonucleotide under conditions that allow linking of the dye phosphoramidite to the oligonucleotide. One skilled in the art can work out the labeling conditions without undue experimentation in view of the disclosure of the present invention.

Those skilled in the art will appreciate that the phosphoramidites of dyes of the present invention can be introduced anywhere in the sequence. The preferred point of addition, however, is the 5'-end of the oligonucleotide, where interference with hybridization by the dye label is minimized. Addition of a second dye is possible by using commercially available linkers thus providing a multi-color labeled oligonucleotide.

This invention provides, therefore, stable and convenient labels for fluorescent detection of biomolecules. The labels can be added to an oligonucleotide in a single automated step on any DNA synthesizer and do not require previously used protection-de-protection steps.

The oligonucleotides labeled with phosphoramidites of dyes of the present invention may be used as fluorescent hybridization probes to identify the presence and quantity of specific complementary nucleotide sequences in samples containing DNA or RNA. Detailed descriptions of these and many other possible applications of cyanine dye labels are provided in the pending U.S. application Ser. No. 09/100,150, entitled "Efficient Activated Cyanine Dyes," U.S. Pat. No. 5,627,027, entitled "Cyanine Dyes as Labeling Reagents for Detection of Biological and Other Materials by Luminescence Methods," U.S. Pat. No. 5,569,587, entitled "Method for Labeling and Detecting Materials Employing Luminescent Arylsulfonate Cyanine Dyes," the relevant contents of which are incorporated herein by reference.

The following examples are intended to illustrate, but not to limit, the scope of the invention. While such examples are typical of those that might be used, other procedures known to those skilled in the art may alternatively be utilized. Indeed, those of ordinary skill in the art can readily envision and produce further embodiments, based on the teachings herein, without undue experimentation.

The general analytical methods and characterization techniques used in these examples are identified below. $^1$H NMR spectra were recorded on a (Bruker) spectrometer at 300 MHz. Chemical shifts were recorded in parts per million ($\delta$) relative to TMS. $^{31}$P NMR spectra were recorded on a (Bruker) spectrometer at 300 MHz. Chemical shifts were recorded in parts per million ($\delta$) relative to phosphoric acid. Analytical reverse phase HPLC analyses were performed on a high pressure liquid chromatography Beckman instrument fitted with a C18 ultrasphere column (5$\mu$ particles,). 46 MM×25 CM (Beckman Cat. #235329).

EXAMPLE 1

Figure 5:
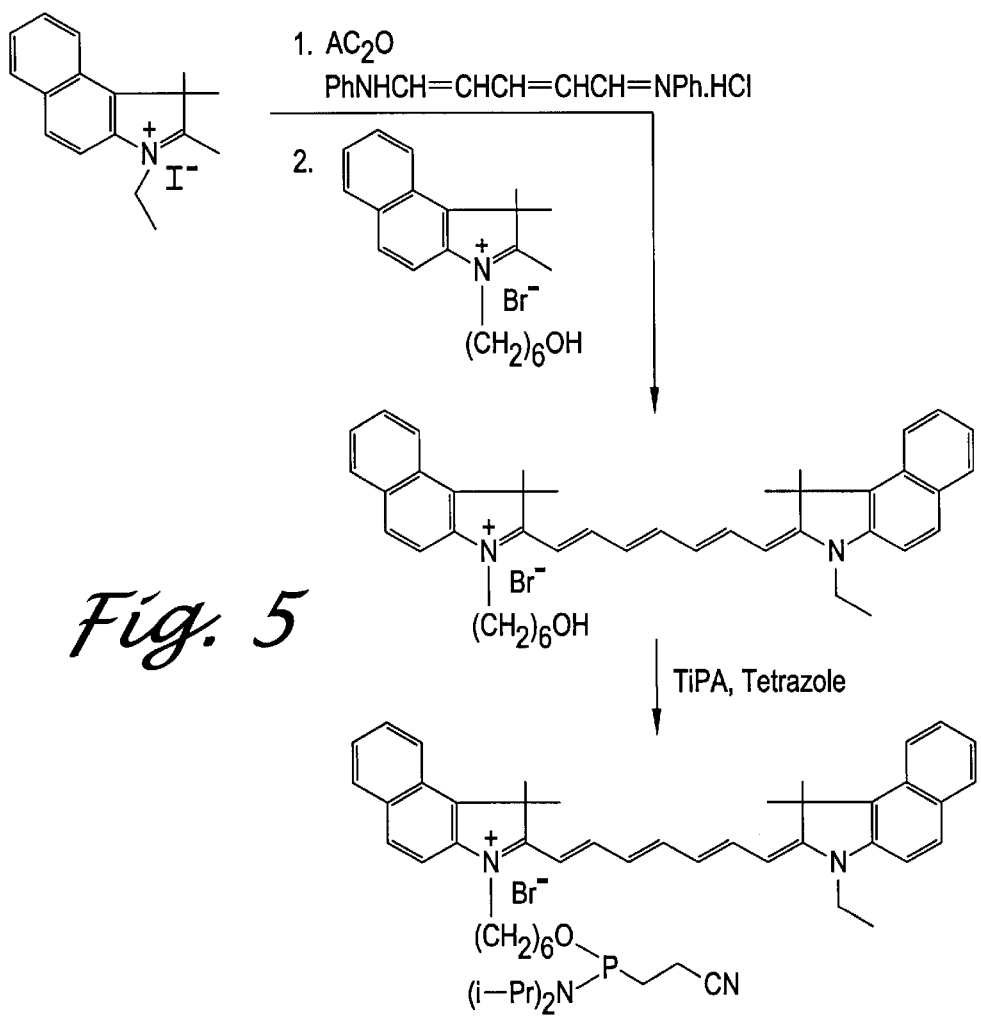
FIG. 5 shows a reaction scheme, illustrating synthesis of DBCy7 phosphoramidite of the present invention.

Synthesis of a Hydroxy Derivative of DBCy5 (FIG. 3) and DBCy7 (FIG. 5)

Figure 4:
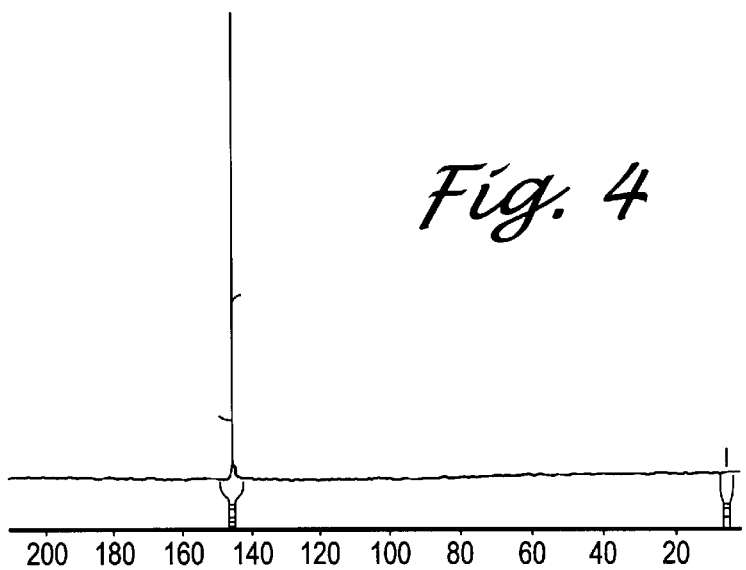
FIG. 4 depicts $^{31}$P NMR spectra of the DBCy5 phosphoramidite obtained according to the reaction scheme of FIG. 3.
Figure 6:
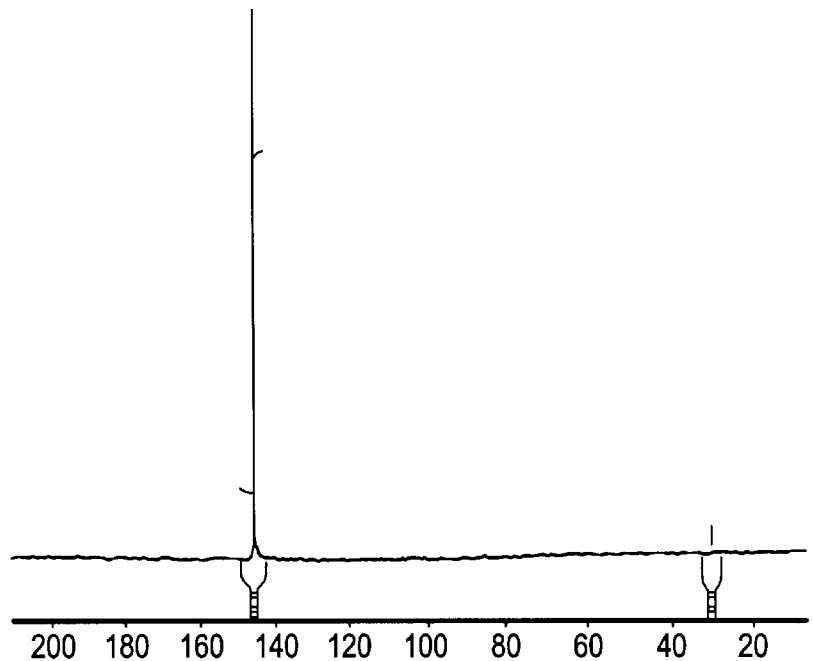
FIG. 6 depicts $^{31}$P NMR spectra of the DBCy7 phosphoramidite obtained according to the reaction scheme of FIG. 5.
Figure 10:
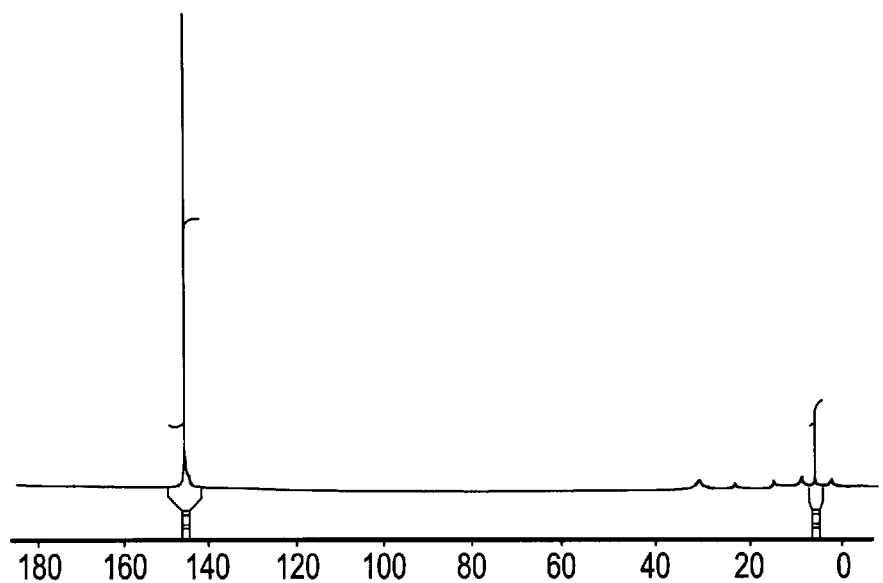
FIG. 10 depicts $^{31}$P NMR spectra of the Cy5 phosphoramidite obtained according to the reaction scheme of FIG. 9.

1-(1'-ethyl)-1,1,2-trimethyl-H-Benz(e)indolinium iodide and the malonaldehyde bis(phenylimine) monohydrochloride (DBCy5), or glutaconaidehydedianil hydrochloride (DBCy7), was heated in acetic anhydride for 30 minutes at 125° C. The resulting intermediate was evaporated to dryness and washed three times with 50 ml of diethyl ether and then reacted with 1-(6-hydroxyhexyl)-1,1,2-trimethyl-H-Benz(e)indolinium bromide in pyridine at 125° C. for 30 minutes. After evaporating the pyridine to dryness, the residue was washed with diethyl ether and purified on silica gel column in $CH_2Cl_2$. Elution with $CH_2Cl_2$/EtOAc/Acetone/MeOH (85/5/5/5) gave 80% yield of DBCy5-OH (FIG. 4) or 60% yield of DBCy7-OH (FIG. 6). The phosphoramidites were characterized by proton NMR (not shown) and $^{31}$P NMR (FIGS. 4 and 6).

EXAMPLE 2

Synthesis of a Hydroxy Derivative of Cyclic Cy7 (FIG. 7) or Cyclic DBCy7 (FIG. 8)

a. Synthesis of 1-Formyl-1-cyclohexene diethyl acetal

To a solution of 1-cyclohexene-1-carboxaldehyde (5.0 g, 45.4 mmole) triethyl orthoformate (13.5 g, 90.8 mmole) in dry ethanol (60 mL) and TsOH (0.0085 g, 2.27 mmole) were added over 3° A molecular sieves (1 g). The reaction was heated to reflux under Argon for 6 hr and then cooled to room temperature. After quenching with solid $NaHCO_3$, the reaction mixture was filtered and concentrated to oil (5.0 g, 60% yield), then used in the next step without further purification.

b. Synthesis of 5-phenylamino-2,4-trimethylene-2,4-pentadiene) phenylammonium chloride To dry dimethyl formamide (DMF) (3.27 g, 44.7 mmole), $POCl_3$ was added, one drop at a time, with vigorous stirring at 0° C. under Argon. After 30 minutes, a solution of 1-formyl-1-cyclohexene diethyl acetal (2.74 g, 14.9 mmole) in DMF (6 mL) was added slowly via a canula. The resulting reaction mixture was stirred at 0° C. for 1 hr, and then at room temperature for 2 hrs. Reaction was cooled to 0° C. and aniline (4.16 g, 44.7 mmole) was added, one drop at a time. After addition of aniline, reaction was warmed to room temperature for 30 min. and then quenched with ice water (100 mL). The reaction mixture was adjusted to pH 10–12 with concentrated NaOH solution and extracted with diethyl ether three times. The combined ether phase was acidified to pH 1–2 with concentrated HCl. Ethanol (10 ml) was added to the mixture, and the mixture was kept at –20° C. for 3 hrs. The precipitate was collected and recrystallized from ethanol, producing purple flakes of the intermediate (3.01 g, 62% yield).

c. Synthesis of hydroxyl derivative of cyclic Cy7 or cyclic DBCy7

1-Ethyl-2,3,3-trimethyl-indolinium iodide or 1-ethyl 1,1,2-trimethyl-H-Benz(e)indolinium iodide (3.00 mmol) and (5-phenylamino-2,4-trimethylene-2,4-pentadiene) phenylammonium chloride (0.975 g, 3.00 mmol) were stirred in $AC_2O$ (50 mL) at 125° C. for one hour. Reaction was cooled to room temperature and concentrated. The residue was washed three times with diethyl ether and dried under vacuum. The resulting intermediate was mixed with 1-(1'-hydroxylhexyl)-2,3,3-trimethyl-indolinium bromide or 1-(1'-hydroxylhexyl)-1,1,2-trimethyl-benz(e)indolinium bromide (3.00 mmol) and pyridine (50 mL) and stirred at 125° C. for 1 hr. Reaction was cooled to room temperature and concentrated. The crude product was washed three times with diethyl ether and purified by flash chromatography (EtOAc, acetone, MeOH, $CH_2Cl_2$. 5:5:5:85 v/v) to yield 46.4% of mono-hydroxylhexyl cyclic Cy7 or 46.7% of mono-hydroxyhexyl Cyclic DBCy7.

EXAMPLE 3

Synthesis of Hydroxy Cy5 (FIG. 9) or Hydroxy DBCy5 (FIG. 11)

A solution of 1-ethyl 2,3,3-trimethyl-(3H)-indolinium iodide (Cy5) or 1-ethyl 1,1,2-trimethyl-H-Benz(e) indolinium iodide (DBCy5) (4.47 mmole) and malonaldehyde bis (phenylamine) monohydro-chloride (8.50 mmole) in a mixture of acetic acid (20 ml) and acetic anhydride (20 ml) was heated in an oil bath preheated to 120° C. for 2 hr. The solvents were removed with a rotary evaporator and the product was washed twice with 30 ml of diethyl ether (total 60 ml of diethyl ether) to remove excess malonaldehyde dianil hydrchloride. The crude product thus obtained was dissolved in an acetic anhydride and pyridine mixture (20 ml/20 ml) and 1-(1'-acetoxypropyl) -2,3,3'trimethyl-(3H)-indolinium iodide (Cy5) or 1-(1'-acetoxypropyl)-1,1,2-trimethyl-HBenz(e)indolinium iodide (DBCy5) (4.47 mmole) was added and the reaction mixture was heated at 110° C. for 30 min. The mixture was cooled and rotary evaporated to remove solvents. The residue was washed with diethylether and dried. The residue was dissolved in 200 ml of 2M HCl in 50:50 water/methanol and stirred overnight at room temperature. The solvent was evaporated and the residue partitioned between $CH_2Cl_2$ and water. The organic layer was dried with sodium sulfate and the solvent was evaporated. The crude product was purified by column chromatography on silica gel, using a mixture of 5/5/5/85 methanol:acetone:ethylacetate:dichloromethane, followed by a 8/8/8/76 mixture of the same components. The appropriate fractions were pooled and evaporated to yield 1 gm (47%) of Cy5-hydroxy and 1.2 gm (56%) of DBCy5-hydroxy compounds.

$^1$H NMR spectra of Cy5-hydroxy was as follows (the chemical shifts are in ppm): 8.02 (dd, 2H, ∃-CH═), 7.4–7.0 (m, 8H, aromatic), 6.9 (t, 1H, (—CH═), 6.58 (d, 1 H, ∀-CH═), 6.21 (d, 1H, ∀-CH═), 4.3 (m, 2H, N—CH$_2$—CH$_3$), 4.1 (m, 2H, N—CH$_2$), 3.87 (m, CH$_2$), 3.6 (s, 1H, —OH), 2.1 (m, 2H, CH$_2$), 1.7 (d, 12H, (CH$_3$)$_4$), and 1.42 (t, 3H, —CH$_2$—CH$_3$).

$^1$H NMR spectra of DBCy5-hydroxy was as follows (the chemical shifts are in ppm): 8.24 (dd, 2H, ∃-CH═), 7.4–8.22 (m, 12H, aromatic), 7.5 (t, 1H, (—CH═), 6.5 (d, 1 H, ∀-CH═), 6.2 (d, 1 H, ∀'-CH═), 4.4 (m, 2H, N—CH$_2$—CH$_3$), 4.1 (m, 2H, N—CH$_2$), 3.9 (m, CH$_2$), 3.7 (s, 1 H, —OH), 2.2 (m, 2H, CH$_2$), 1.94 (d, 12H, (CH$_3$)$_4$), and 1.4 (t, 3H, —CH$_2$—CH$_3$).

EXAMPLE 4

Synthesis of a Hydroxy Derivative of Cyclic Cy7 (FIG. 13)

Figure 14:
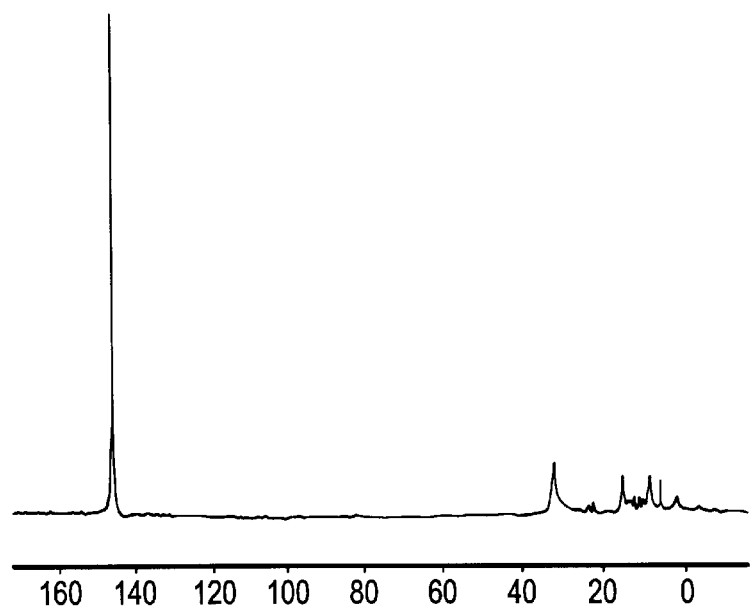
FIG. 14 depicts $^{31}$P NMR spectra of the cyclic Cy7 phosphoramidite obtained according to the reaction scheme of FIG. 13.

1-(1'-acetoxypropyl)-2,3,3-trimethyl-(3H)-indolinium iodide (774 mg, 2 mmole), bisaldehyde (345 mg, 2 mmole), 1-(1'-ethyl)-2,3,3-trimethyl indolinium iodide (630.40 mg, 2 mmole), and sodium acetate (328.12 mg, 4 mmole) were mixed in a round bottom flask. 24 ml of AcOH and 18 ml of AC$_2$O were added to the mixture. The reaction mixture was heated at 100° C. for 60 minutes. The progress of the reaction was monitored by UV-VIS at 778 nm. The reaction mixture was cooled to room temperature. The solvents were evaporated under vacuum to dryness. The residue was washed three times with 50 ml of diethyl ether (total of 150 ml) to yield 1.16 gm (74%) of the product. 1.16 g of the obtained compound was placed in a round bottom flask and 60 ml of anhydrous DMF and NaSC$_2$H$_5$ (20 equivalents) were added. The reaction mixture was heated and incubated at 100–110° C. for 2–3 hours. The progress of the reaction was monitored by UV-VIS at 748 nm. The reaction mixture was cooled and evaporated to dryness under vacuum. The obtained residue was triturated with CHCl$_3$. The residue was purified on silica gel column in CH$_2$Cl$_2$. Elution with CH$_2$Cl$_2$/EtOAc/Acetone/MeOH (85/5/5/5) yielded 0.231 gm (22%) of the desired product. The cyclic Cy7-phosphoramidite was characterized by proton NMR and $^{31}$P NMR (FIG. 14).

EXAMPLE 5

Figure 15A:
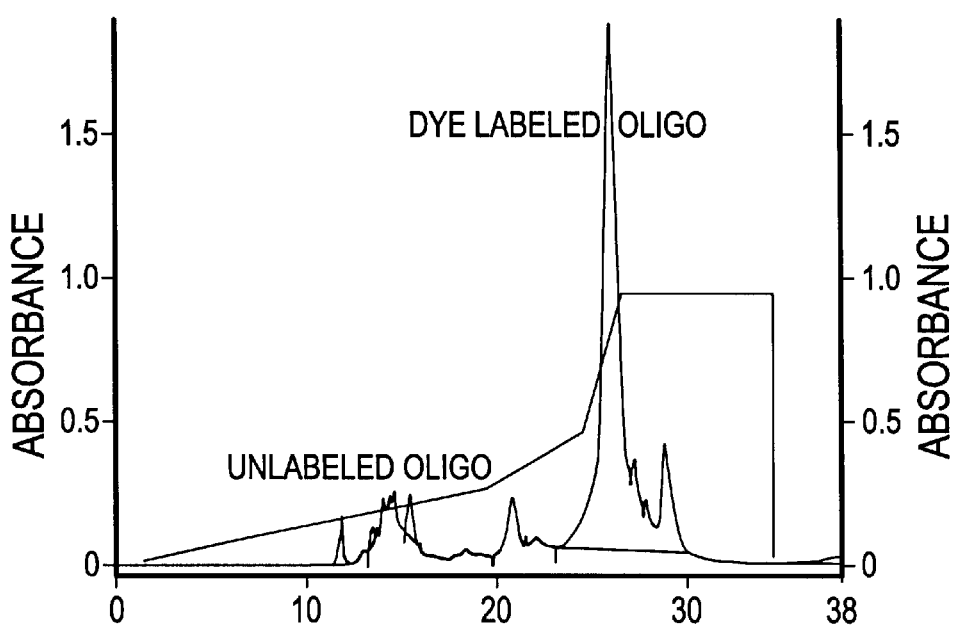
FIGS. 15(A) and 15(B) show HPLC chromatograms of an oligonucleotide labeled with the dye phosphoramidite of the present invention before (FIG. 15(A)) and after (FIG. 15(B)) purification.
Figure 15B:
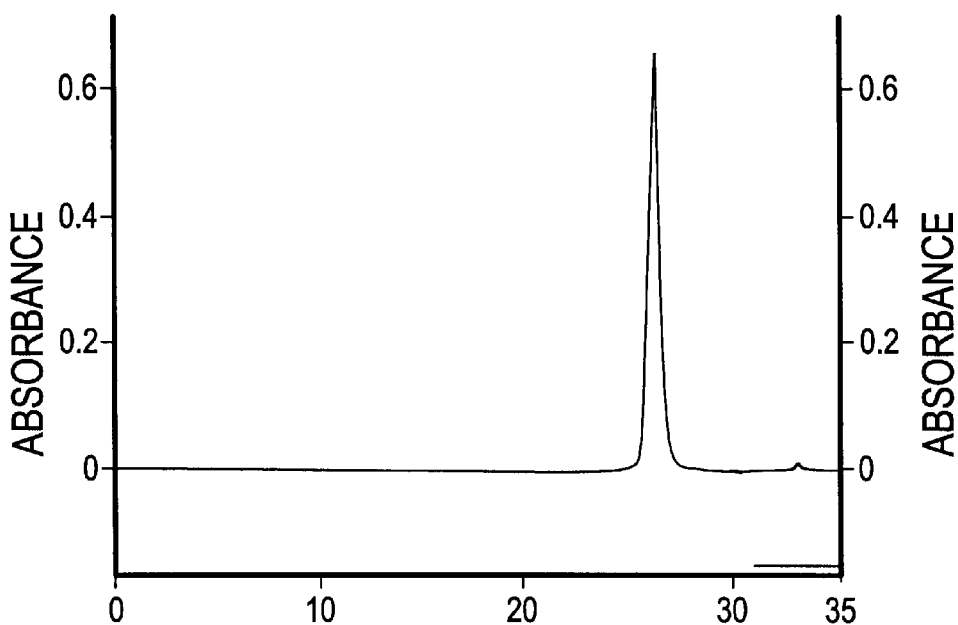

Coupling of Dye Phosphoramidites of the Present Invention to Oligonucleotides The desired labeled oligonucleotide was obtained using A$^{pac}$, G$^{ipr-pac}$, C$^{ac}$ and T phosphoramidite on an automated DNA synthesizer (oligo 1000 M or ABI 392). 100 mg of the dye phosphoramidite was dissolved in 1 ml of acetonitrile (0.1 M solution) and placed in the DNA synthesizer. The dye phosphoramidite was coupled for 10 minutes. After the synthesis, the oligonucleotide was cleaved and deprotected using NH$_4$OH or 0.05 M K$_2$CO$_3$/MeOH for two hours at room temperature. The obtained solution was evaporated on speed VAC. The labeled oligonucleotide was isolated by reverse phase HPLC (Beckman HDLL Gold System) using a C18 column. Buffers A (0.1 M NH$_4$OAc, pH 7.0) and B (100% acetonitrile) were used. Gradients of 0–50% B in A were employed: 0–20 min gradient to 15%B, 20–25 min gradient to 25%B, 25–32 min gradient to 50%B, 32–37 min 50%B, 37–38 min 0%B (FIGS. 15A and 15B). The elute from HPLC was evaporated to complete dryness and then dissolved in water. Absorbency of the solution was measured on Beckman DU-70 spectrophotometer at 260 nm and 650 mn and was found to be consistent with the cyanine dye-labeled oligonucleotide (not shown). The presence of the purified labeled oligonucleotide was also confirmed by Capillary Electrophoresis (CE), Beckman PACE 5000 equipped with LIF detector, CEQ2000), and HPLC.

What is claimed is:

1. A dye phosphoramidite having a formula:

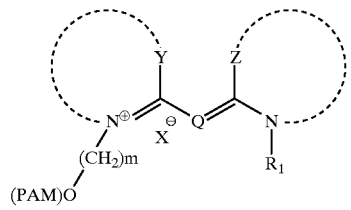

wherein:

each dotted line represents carbon atoms necessary to form a fused substituted or unsubstituted aromatic ring or rings;

m is an integer from 1 to 18;

Y and Z are independently selected from the group consisting of S, O, N, CH$_2$ and C(CH$_3$)$_2$;

R$_1$ is an alkyl;

(PAM) is a phosphoramidite group;

X$^⊖$ is a negative ion; and

Q is

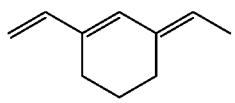

2. The dye phosphoramidite of claim 1, wherein said aromatic ring is phenyl, naphthyl, or heterocyclic ring.

3. The dye phosphoramidite of claim 1, wherein said alkyl possesses 1 to 18 carbon atoms.

4. The dye phosphoramidite of claim 3, wherein said alkyl is ethyl.

5. The dye phosphoramidite of claim 1, wherein said dye is a cyanine dye.

6. The dye phosphoramidite of claim 5, wherein said cyanine dye is selected from the group consisting of cyclic Cy7, cyclic benz Cy7, and cyclic dibenz Cy7.

7. The dye phosphoramidite of claim 1, wherein said negative ion is $I^{\ominus}$ or $Br^{\ominus}$.

8. The dye phosphoramidite of claim 1, wherein said phosphoramidite group is a N,N-diisopropyl-O-β-cyanoethyl phosphoramidite group.

9. The dye phosphoramidite of claim 1, wherein n=2, the dye is Cy5, BCy5, or DBCy5 and Q is

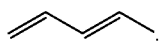

10. The dye phosphoramidite of claim 1, wherein n=3, the dye is Cy7, BCy7, or DBCy and Q is

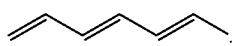

11. The dye phosphoramidite of claim 1, wherein the dye is cyclic Cy7, cyclic BCy7, or cyclic DBCy and Q is

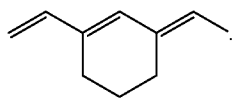

12. A method of synthesizing a dye phosphoramidite comprising the steps of:

(a) forming a hydroxy derivative of the dye having a formula:

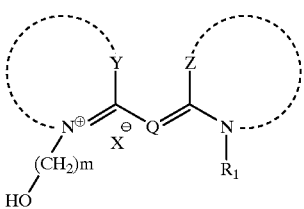

wherein each dotted line represents carbon atoms necessary to form a fused substituted or unsubstituted aromatic ring; m is an integer from 1 to 18; Y and Z are independently selected from the group consisting of S, O, N, $CH_2$ and $C(CH_3)_2$; $R_1$ is an alkyl; $X^{\ominus}$ is a negative ion; and Q is

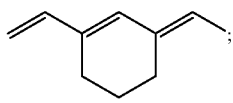

and (b) replacing hydrogen of the OH group with a phosphoramidite group.

13. The method of claim 12, wherein said aromatic ring is phenyl, naphthyl, or heterocyclic ring.

14. The method of claim 12, wherein said alkyl possesses 1 to 12 carbon atoms.

15. The method of claim 14, wherein said alkyl is ethyl.

16. The method of claim 12, wherein said negative ion is $I^{\ominus}$ or $Br^{\ominus}$.

17. The method of claim 12, wherein said phosphoramidite group is a N,N-diisopropyl-O-β-cyanoethyl phosphoramidite group.

18. The method of claim 12, wherein said dye is a cyanine dye.

19. The dye phosphoramidite of claim 18, wherein said cyanine dye is selected from the group consisting of cyclic Cy7, cyclic benz Cy7, and cyclic dibenz Cy7.

20. The method of claim 12, wherein the step of forming a hydroxy derivative of the dye comprises reacting compounds (XI), (XII), and (XIII) under conditions that allow the formation of the hydroxy derivative of the dye, wherein Compound (XI) having a formula:

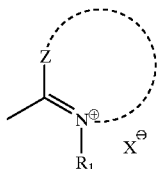

Compound (XII) having a formula: Ph—$R_3$—Ph, wherein Ph is phenyl and
$R_3$ is:

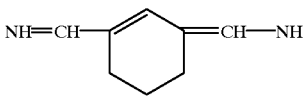

Compound (XIII) having a formula:

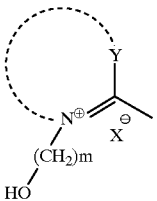

herein each dotted line represents carbon atoms necessary to form a fused substituted or unsubstituted aromatic ring; m is an integer from 1 to 18; Y and Z are independently selected from the group consisting of S, O, N, $CH_2$ and $C(CH_3)_2$; $R_1$ is an alkyl; and $X^{\ominus}$ is a negative ion.

21. The method of claim 20, wherein said aromatic ring is phenyl, naphthyl, or heterocyclic ring.

22. The method of claim 20, wherein said negative ion is Br$^{\ominus}$.

23. The method of claim 20, wherein said alkyl possesses 1 to 18 carbon atoms.

24. The method of claim 23, wherein said alkyl is ethyl.

25. The method of claim 20, wherein Compound (XIII) is formed by reacting Compound (XIV) with Br(CH$_2$)$_m$—OH under reaction conditions that allow the formation of compound (XIII), Compound (XIV) having a formula:

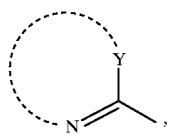

wherein dotted line represents carbon atoms necessary to form a fused substituted or unsubstituted aromatic ring; Y is selected from the group consisting of S, O, N, CH$_2$ and C(CH$_3$)$_2$; and m is an integer from 1 to 18.

26. The method of claim 20, wherein the dye is cyclic Cy7, Compound (XI) is 1-ethyl-2,3,3-trimethyl-(3H)-indolinium iodide, and Compound (XIII) is 1-(6-hydroxyhexyl)-1,1,2-trimethyl-(3H)-indolinium bromide.

27. The method of claim 20, wherein the dye is cyclic DBCy7, Compound (XI) is 1-ethyl-1,1,2-trimethyl-H-Benz (e)indolinium iodide and Compound (XIII) is 1-(6-hydroxyhexyl)-1,1,2-trimethyl-H-Benz(e)indolinium bromide.

28. The method of claim 12, wherein the step of forming a hydroxy derivative of the dye comprises:

(a1) forming an acetoxy derivative of the dye having a formula:

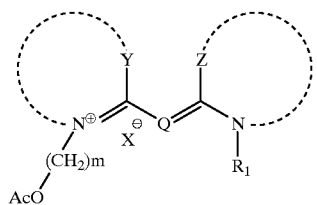

wherein each dotted line represents carbon atoms necessary to form a fused substituted or unsubstituted aromatic ring; m is an integer from 1 to 18; Y and Z are independently selected from the group consisting of S, O, N, CH$_2$ and C(CH$_3$)$_2$; R$_1$ is an alkyl; X$^{\ominus}$ is a negative ion; and Q is

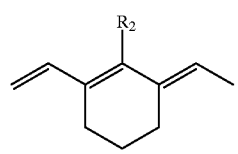

wherein R$_2$ is a halogen or hydrogen; and
(a2) converting AcO group of the dye into the OH group.

29. The method of claim 28, wherein said aromatic ring is phenyl, naphthyl, or heterocyclic ring.

30. The method of claim 28, wherein said alkyl possesses 1 to 12 carbon atoms.

31. The method of claim 30, wherein said alkyl is ethyl.

32. The method of claim 28, wherein said dye is a cyanine dye.

33. The dye phosphoramidite of claim 5, wherein said cyanine dye is selected from the group consisting of cyclic Cy7, cyclic benz Cy7, and cyclic dibenz Cy7.

34. The method of claim 28, wherein said negative ion is I$^{\ominus}$.

35. The method of claim 28, wherein said halogen is chlorine.

36. The method of claim 28, wherein the step of forming the acetoxy derivative of the cyanine dye comprises reacting compounds (XI), (XXII) and (XXIII) under conditions that allow forming of the acetoxy derivative of the dye, Compound (XI) having a formula:

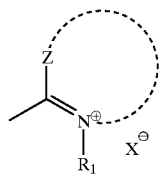

Compound (XXII) having a formula:

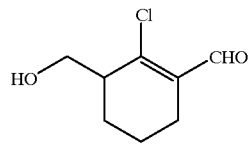

Compound (XXIII) having a formula:

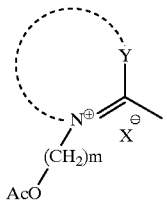

wherein each dotted line represents carbon atoms necessary to form a fused substituted or unsubstituted aromatic ring; m is an integer from 1 to 18; Y and Z are independently selected from the group consisting of S, O, N, CH$_2$ and C(CH$_3$)$_2$; R$_1$ is an alkyl; and X$^{\ominus}$ is a negative ion.

37. The method of claim 36 wherein said aromatic ring is phenyl, naphthyl, or heterocyclic ring.

38. The method of claim 36 wherein said negative ion is I$^{\ominus}$.

39. The method of claim 36 wherein said alkyl possesses 1 to 12 carbon atoms.

40. The method of claim 39 wherein said alkyl is ethyl.

41. The method of claim 36 wherein the cyanine dye is cyclic Cy7, Compound (XI) is 1-ethyl-2,3,3-trimethyl-(3H)-indolinium iodide, and Compound (XXIII) is 1-(1'-acetoxypropyl)-2,3,3'-trimethyl-(3H)-indolinium iodide.

42. The method of claim 36 wherein the cyanine dye is cyclic DBCy7, Compound (XI) is 1-ethyl-1,1,2-trimethyl-H-Benz(e)indolinium iodide, and Compound (XXIII) is 1-(1'-acetoxypropyl)-2,3,3'-trimethyl-H-Benz(e)indolinium iodide.

43. A method of labeling an oligonucleotide, comprising:
reacting the dye phosphoramidite of claim 1 with the oligonucleotide under conditions that allow linking of the dye to the oligonucleotide.

* * * * *